(12) United States Patent
Cho et al.

(10) Patent No.: US 10,036,751 B2
(45) Date of Patent: Jul. 31, 2018

(54) METHOD OF EVALUATING GLIOBLASTOMA MULTIFORME PATIENT APPLICABLE TO IMMUNOTHERAPY TREATMENT BASED ON DENDRITIC CELL TUMOR VACCINES AND METHOD OF PROGNOSTICATING SURVIVAL RATE IN GLIOBLASTOMA MULZTIFORME PATIENT AFTER TREATMENT

(71) Applicant: China Medical University Hospital, Taichung (TW)

(72) Inventors: Der-Yang Cho, Taichung (TW); Shao-Chih Chiu, Taichung (TW); Chia-Ing Jan, Taichung (TW)

(73) Assignee: China Medical University Hospital, Taichung, (TW)

( * ) Notice: Subject to any disclaimer, the term of this patent is extended or adjusted under 35 U.S.C. 154(b) by 25 days.

(21) Appl. No.: 15/155,089

(22) Filed: May 16, 2016

(65) Prior Publication Data

US 2017/0045516 A1   Feb. 16, 2017

(30) Foreign Application Priority Data

Aug. 10, 2015   (TW) .............................. 104125986 A

(51) Int. Cl.
G01N 33/574   (2006.01)

(52) U.S. Cl.
CPC ..... *G01N 33/57407* (2013.01); *G01N 33/574* (2013.01); *G01N 2333/70503* (2013.01); *G01N 2333/70517* (2013.01); *G01N 2333/70532* (2013.01); *G01N 2800/52* (2013.01)

(58) Field of Classification Search
None
See application file for complete search history.

(56) References Cited

FOREIGN PATENT DOCUMENTS

WO   2015116868 A2   8/2015

OTHER PUBLICATIONS

Brendan Fong et al., "Monitoring of regulatory T cell frequencies and expression of CTLA-4 on T cells, before and after DC vaccination, can predict survival in GBM patients", PLOS ONE, published on Apr. 2, 2012, vol. 7, issue 1, pp. 1-9, published by Public Library of Science, United States.
Jennifer S. Sims et al., "Biomarkers for glioma immunotherapy: the next generation", Journal of Neuro-Oncology, published in Jul. 2015, vol. 123, issue 3, pp. 1-23, published by Springer US, United States.
Carmen Visus et al., "Potential of immune biomarkers for predicting survival in glioblastoma patients receiving dendritic cell cancer immunotherapy VAC12P.1012", The Journal of Immunology, published on May 1, 2014, vol. 192, issue 1 supplement 206.1, pp. 1-2, published by the American Association of Immunologists, Inc., United States.
Joseph P. Antonios et al., "Dendritic cell immunotherapy for brain tumors", Journal of Neuro-Oncology, published in Jul. 2015, vol. 123, issue 3, pp. 425-432, published by Springer US, United States.
Bo Wei et al., "The upregulation of programmed death 1 on peripheral blood T cells of glioma is correlated with disease progression", Tumor Biology, published in Apr. 2014, vol. 35, issue 4, pp. 2923-2929, published by Springer Netherlands, Netherlands.
Edjah K.Nduom et al., "PD-L1 expression and prognostic impact in glioblastoma", Neuro-Oncology, published in Feb. 2016, vol. 18, issue 2, pp. 195-205, published by Oxford University Press, United Kingdom.
Yawei Liu et al., "PD-L1 expression by neurons nearby tumors indicates better prognosis in glioblastoma patients", Journal of Neuroscience, published on Aug. 28, 2013, vol. 33, issue 35, pp. 14231-14245, published by Society for Neuroscience, United States.
Christopher J. Wheeler et al., "Thymic CD8+ T Cell Production Strongly Influences Tumor Antigen Recognition and Age-Dependent Glioma Mortality", The Journal of Immunology, published on Nov. 1, 2003, vol. 171, issue 9, pp. 4927-4933, published by the American Association of Immunologists, Inc., United States.
Christopher J. Wheeler et al., "Clinical Responsiveness of Glioblastoma Multiforme to Chemotherapy after Vaccination", Clinical Cancer Research, published on Aug. 15, 2004, vol. 10, issue 16, pp. 5316-5326, published by The American Association for Cancer Research, Inc., United States.
S Han et al., "Tumour-infiltrating CD4+ and CD8+ lymphocytes as predictors of clinical outcome in glioma", British Journal of Cancer, published on May 13, 2014, vol. 110, issue 10, pp. 2560-2568, published by Nature Publishing Group on behalf of Cancer Research UK, England.
Courtney A. Crane et al., "Individual Patient-Specific Immunity Against High-Grade Glioma after Vaccination with Autologous Tumor Derived Peptides Bound to the 96 KD Chaperone Protein", Clinical Cancer Research, published on Jan. 1, 2013, vol. 19, issue 1, pp. 205-214, published by the American Association for Cancer Research, Inc., United States.

*Primary Examiner* — Nelson B Moseley, II
(74) *Attorney, Agent, or Firm* — CKC & Partners Co., Ltd.

(57) ABSTRACT

A method of evaluating if a glioblastoma multiforme (GBM) patient is applicable to be treated with an immunotherapy based on dendritic cell tumor vaccines includes a sample obtaining step to obtain a sample from the GBM patient, a detecting step to detect an expression level of a biomarker, and a comparing step to compare the expression level of the biomarker to a threshold, wherein the GBM patient is applicable to treat with the immunotherapy based on dendritic cell tumor vaccines when the expression level of the biomarker is lower than the threshold. A method of prognosticating a survival rate in the GBM patient after a treatment includes a sample obtaining step, a detecting step, and a comparing step, wherein the GBM patient is determined to have a good prognosis after the treatment when the expression level of the sample from the GBM is lower than the threshold.

5 Claims, 18 Drawing Sheets
(2 of 18 Drawing Sheet(s) Filed in Color)

METHOD OF EVALUATING GLIOBLASTOMA MULTIFORME PATIENT APPLICABLE TO IMMUNOTHERAPY TREATMENT BASED ON DENDRITIC CELL TUMOR VACCINES AND METHOD OF PROGNOSTICATING SURVIVAL RATE IN GLIOBLASTOMA MULZTIFORME PATIENT AFTER TREATMENT

RELATED APPLICATIONS

This application claims priority to Taiwan Application Serial Number 104125986, filed Aug. 10, 2015, which is herein incorporated by reference.

BACKGROUND

Technical Field

The present disclosure relates to a method of evaluating a cancer patient who is applicable to be treated with an immunotherapy and the method of prognosticating a survival rate for the cancer patient after a treatment. More particularly, the present disclosure relates to the method of evaluating a glioblastoma multiforme patient who is applicable to be treated with an immunotherapy based on a dendritic cell tumor vaccine and the method of prognosticating the survival rate in the glioblastoma multiforme patient after the treatment.

Description of Related Art

A glioblastoma multiforme (GBM) is an astrocytoma of a glioma, as known as Grade IV Astrocytoma in the WHO classification. The GBM is the most commonly and the most aggressive malignant primary brain tumor in humans.

Conventional practices for GBM treatments involve a surgery, a radiation therapy and a chemotherapy. Glial cells in a brain are a kind of the constituent units of a nervous system, glial cells tightly cover axons and provide functions such as support, nutrition supplement, constant environment maintenance and insulation. However, because the axon is very long, the tumor cells will spread along the axon to a distant place once the glial cells become cancerous; that is, the GBM has a very high infiltration, which refers to a migration of cells from their sources to other place. The surgery could not remove a distant infiltration part of the tumor cells, and therefore the chemotherapy and/or the radiotherapy is needed for killing residual tumor cells in the distant infiltration part after the surgery. However, the presence of cancer stem cells having a radioresistance and chemoresistance causes a high recurrence rate after such treatments.

In recent years, some biomarkers have been used to diagnose cancers, determine adjuvant therapies, or estimate prognoses in patients besides general checkups and traditional clinical stages. For example, estrogen receptor (ER) and epidermal growth factor receptor 2 (HER2) are used as biomarkers for choosing therapeutic drugs in the diagnosis and the treatment of breast cancer. Because of the high malignancy, high recurrence rate after treatments, and high death rate, it is important to develop a method for treating the GBM, or the method for predicting a survival rate in the patient after the treatment. Therefore, physicians can prepare more appropriate treatment plans for individual patients in clinical to improve the survival rate after the treatment.

SUMMARY

According to one aspect of the present disclosure, a method of evaluating a glioblastoma multiforme patient who is applicable to an immunotherapy treatment based on a dendritic cell tumor vaccine includes steps as follows. A sample obtaining step is provided, wherein a sample is obtained from the glioblastoma multiforme patient. A detecting step is provided, wherein an expression level of a biomarker is detected and then the expression level is calculated as a base value, in which the biomarker is selected from a group consisting of PD-1, PD-L1, CD8, and a combination thereof. A comparing step is provided, wherein the base value is compared with a threshold. The glioblastoma multiforme patient is applicable to be treated with the immunotherapy treatment based on the dendritic cell tumor vaccine when the base value is lower than the threshold.

According to other aspect of the present disclosure, a method of prognosticating a survival rate in a glioblastoma multiforme patient after a treatment includes steps as follows. A sample obtaining step is provided, wherein a sample is obtained from the glioblastoma multiforme patient. A detecting step is provided, wherein an expression level of a biomarker is detected and then the expression level is calculated as a base value, in which the biomarker is selected from a group consisting of PD-1, PD-L1, CD8, and the combination thereof. A comparing step is provided, wherein the base value is compared with a threshold. The glioblastoma multiforme patient is determined to have a good prognosis after the treatment when the base value is lower than the threshold.

BRIEF DESCRIPTION OF THE DRAWINGS

The patent or application file contains at least one drawing executed in color. Copies of this patent or patent application publication with color drawing(s) will be provided by Office upon request and payment of the necessary fee. The present disclosure can be more fully understood by reading the following detailed description of the embodiment, with reference made to the accompanying drawings as follows.

DETAILED DESCRIPTION

A method of evaluating a glioblastoma multiforme (GBM) patient who is applicable to be treated with an immunotherapy treatment based on a dendritic cell tumor vaccine and the method of prognosticating a survival rate in the GBM patient after a treatment are provided. An expression level of a biomarker of a sample from the GBM patient is detected by an immunohistochemistry. The expression level of the biomarker is performed a semi-quantitative analysis by a H-score method or an image processing method to evaluate whether the GBM patient is applicable to be treated with the immunotherapy treatment based on the dendritic cell tumor vaccine, and prognosticate the survival rate in the GBM patient after the treatment. The following are descriptions of the specific terms used in the specification:

The term "biomarker" refers to a substance which is capable of indicating certain biological states or conditions. The biomarker can be used as an indicator to evaluate or objectively measure normal biological processes, pathogenic processes, or responses to a treatment.

The term "PD-1 (programmed cell death-1)", also known as CD279 (duster of differentiation 279), is a protein that in humans is encoded by a PDCD1 gene. The PD-1 is a cell surface receptor that belongs to an immunoglobulin superfamily and is expressed on T cells and pro-B cells.

The term "PD-L1 (programmed cell death-1)", also known as CD274 (duster of differentiation 274) or B7-H1 (B7 homolog 1), is a protein that in humans is encoded by a CD274 gene. The PD-L1 is a 40 kDa type 1 transmembrane protein that has been speculated to play a major role in suppressing the immune system during particular events such as pregnancy, tissue allografts, autoimmune disease and other disease states such as hepatitis. The PD-L1 can be transmitted by an inhibitory immunoreceptor through transmitting a signal of a negative regulation to partially suppress immune responses and maintain an immune tolerance of peripheral systems, wherein the PD-1 is one of inhibitory immunoreceptors. Normally an immune system reacts to foreign antigens where is some accumulation in lymph nodes or spleen, which triggers a proliferation of antigen-specific $CD8^+$ T cells. The formation of PD-1/PD-L1 complex transmits an inhibitory signal which reduces the proliferation of these $CD8^+$ T cells at the lymph nodes and supplementary to that the PD-1 is also able to control the accumulation of foreign antigen specific T cells in the lymph nodes through regulation of Bcl-2 gene.

The term "CD8 (cluster of differentiation 8)" is a transmembrane glycoprotein. The CD8 is a cell surface marker of cytotoxic T cells that serves as a co-receptor for the T cell receptor (TCR). The CD8 binds to a major histocompatibility complex (MHC) molecule, and is specific for the class I MHC protein.

Figure 1:
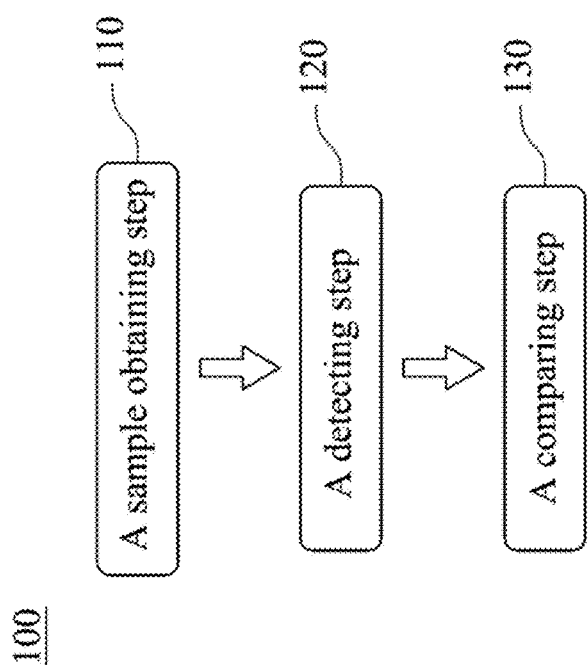
FIG. 1 is a flow diagram showing a method of evaluating a glioblastoma multiforme (GBM) patient applicable to treat with an immunotherapy treatment based on a dendritic cell tumor vaccine according to one embodiment of the present disclosure.

FIG. 1 is a flow diagram showing the method of evaluating the GBM patient who is applicable to be treated with an immunotherapy treatment based on the dendritic cell tumor vaccine according to one embodiment of the present disclosure. In FIG. 1, the method of evaluating the GBM patient who is applicable to be treated with an immunotherapy treatment based on the dendritic cell tumor vaccine 100 includes a sample obtaining step 110, a detecting step 120, and a comparing step 130.

First, the sample obtaining step 110 is provided, wherein the sample is obtained from the GBM patient. The sample can be a tumor tissue or a blood, wherein the tumor tissue can be a frozen tissue section, a paraffin-embedded tissue section, or a tissue microarray.

Second, the detecting step 120 is provided, wherein the expression level of a biomarker is detected and then the expression level of the biomarker is calculated as a base value. In more details, the biomarker is selected from a group consisting of PD-1, PD-L1, CD8, and a combination thereof. The expression level of the biomarker is detected by the immunohistochemistry, and then the expression level of the biomarker is performed the semi-quantitative analysis by an H-score method or an image processing method to calculate a signal value. When the expression level of the PD-1 and the expression level of the PD-L1 are measured, the base value is the signal value measured in the semi-quantitative analysis. When the ratio of the expression level of the PD-1 to the expression level of the CD8 is measured, the base value is the ratio of the signal value of the PD-1 expression level to the signal value of the CD8 expression level. The image processing method can use a RGB (red/green/blue) color model, a CMYK (cyan/magenta/yellow/key) color model or a HSI (hue/saturation/intensity) color model to analyze an image of the sample.

Finally, the comparing step 130 is provided, wherein the base value is compared with a threshold. The GBM patient is applicable to be treated with the immunotherapy treatment based on the dendritic cell tumor vaccine when the base value is lower than the threshold. The threshold will be adjusted according to the method of calculating the base value in the detection step.

Figure 2:
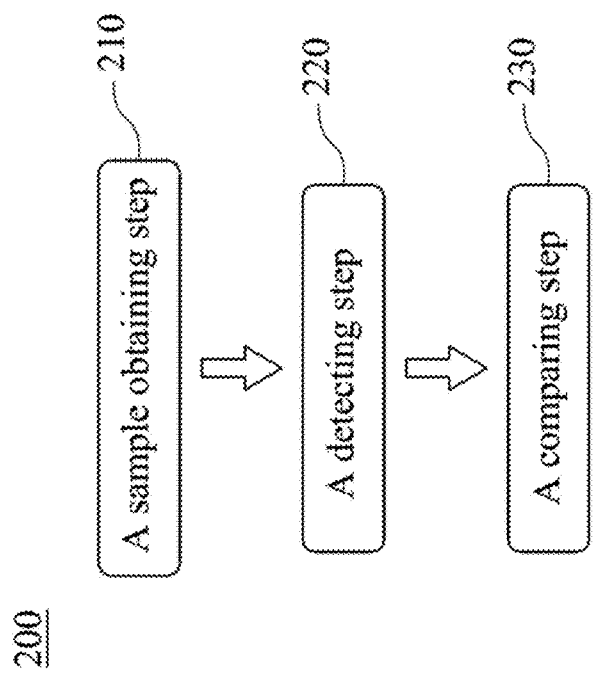
FIG. 2 is a flow diagram showing the method of prognosticating a survival rate in the GBM patient after a treatment according to another embodiment of the present disclosure.

FIG. 2 is a flow diagram showing the method of prognosticating a survival rate in the GBM patient after the treatment according to another embodiment of the present disclosure. In FIG. 2, the method of prognosticating the survival rate in a glioblastoma multiforme patient after a treatment includes the sample obtaining step 210, the detecting step 220, and the comparing step 230.

The sample obtaining step 210 is provided, wherein the sample is obtained from the GBM patient. The sample can be the tumor tissue or the blood, wherein the tumor tissue can be the frozen tissue section, the paraffin-embedded tissue section, or the tissue microarray.

The detecting step 220 is provided, wherein the expression level of the biomarker is measured and then the expression level of the biomarker is calculated as the base value. In more details, the biomarker is selected from a group consisting of PD-1, PD-L1, CD8, and the combination thereof. The expression level of the biomarker is detected by the immunohistochemistry, and then the expression level of the biomarker is performed the semi-quantitative analysis by the H-score method or the image processing method to calculate the signal value. When the expression level of the PD-1 and the expression level of the PD-L1 are measured, the base value is the signal value measured in the semi-quantitative analysis. When the ratio of the expression level of the PD-1 to the expression level of the CD8 is measured, the base value is the ratio of the signal value of the PD-1 expression level to the signal value of the CD8 expression level. The image processing method can use the RGB (red/green/blue) color model, the CMYK (cyan/magenta/yellow/key) color model or the HSI (hue/saturation/intensity) color model to analyze the image of the sample.

The comparing step 230 is provided, wherein the base value is compared with the threshold. The GBM patient is determined to have a good prognosis after the treatment when the base value is lower than the threshold. The threshold will be adjusted according to the method of calculating the base value in the detection step. The treatment can be selected from a group consisting of a surgery, a radiotherapy, a chemotherapy, an immunotherapy, and the combination thereof. In particular, the immunotherapy can be based on the dendritic cell tumor vaccine.

Reference will now be made in detail to the present embodiments of the present disclosure, examples of which are illustrated in the accompanying drawings. Wherever possible, the same reference numbers are used in the drawings and the description to refer to the same or like parts.

EXAMPLES

I. The GBM Patient

This clinical trial program is approved by China Medical University & Hospital Research Ethics Committee, wherein subjects are the GBM patients. The clinical trial program tracks the GBM patient's conditions ten years.

There are 35 patients with diagnosed the GBM participating in this clinical trial program during 2005-2014. An age distribution of the GBM patients ranges from 27 years to 78 years (mean 50.97 years). Table 1 shows clinical features of the GBM patients. The variables in this clinical trial program are a gender, an age and the treatment, wherein the treatment includes the radiotherapy, the chemotherapy, the surgery, a concurrent chemoradiotherapy, and the immunotherapy. In terms of the gender as the variable, there are 17 patients are male and 18 patients are female in 35 GBM patients. In terms of the age as the variable, there are 8 patients are older than or equal to 60 years old, and 27 patients are younger than 60 years old. In terms of the treatment as the variable, there are 26 patients treated with the radiotherapy, 23 patients treated with the chemotherapy, 10 patients treated with the surgery, 14 patients treated with the concurrent chemoradiotherapy, and 21 patients treated with the immunotherapy in 35 GBM patients.

TABLE 1

The clinical features of the GBM patients

| Variable | Number | Percentage (%) |
|---|---|---|
| Gender | | |
| Male | 17 | 48.57 |
| Female | 18 | 51.43 |
| Age (years) | | |
| ≥60 | 8 | 22.86 |
| <60 | 27 | 77.14 |
| Treatment Radiotherapy | | |
| No | 9 | 25.71 |
| Yes | 26 | 74.29 |
| Temozolomide | | |
| No | 12 | 34.29 |
| Yes | 23 | 65.71 |
| Gamma Knife Surgery | | |
| No | 25 | 71.43 |
| Yes | 10 | 33.33 |
| Concurrent Chemoradiotherapy | | |
| No | 19 | 57.48 |
| Yes | 14 | 42.42 |
| Autologous Dendritic Cell/Tumor Antigen Immunotherapy | | |
| No | 14 | 40 |
| Yes | 21 | 60 |

II. Expression Level of the Biomarker Detected by the Immunohistochemistry

1. The Sample is the Tumor Tissue

The sample in this example is the tumor tissue. The tumor tissue from the GBM patient is obtained by conventional biopsy manners. The tumor tissue can be the frozen tissue sections, the paraffin-embedded tissue sections, or the tissue microarray. The samples are performed the immunohistochemistry to detect the expression levels of the biomarkers of the PD-1, the PD-L1, and the CD8.

The immunohistochemistry is performed as follows steps. If the sample is a paraffin-embedded tissue, the paraffin-embedded tissue section with 1-2 μm thickness is put on a slide coating with organosilane. To facilitate subsequent immunohistochemistry, the paraffin-embedded tissue section is then dried overnight (50-55° C.) to dissolve the paraffin and strengthen an adhesion between the slide and the tissue section. Before the immunohistochemistry, the paraffin-embedded tissue section is performed a deparaffinization step to remove the paraffin in the tissue and intercellular spaces, and then performed the immunohistochemistry. If the sample is the frozen tissue section, the frozen tissue section with 2-4 μm thickness is performed the immunohistochemistry directly. Primary antibodies used in the immunohistochemistry are PD-1 (Leica), PD-L1 (Abcam), and CD8 (Leica), and a dilution is 1:200, 1:100, and 1:100 respectively. The tissue section is retrieved by EDTA buffer solution at 100° C. for 20 minutes, and then hybridized with the primary antibody at room temperature for 1 hour. The tissue section is conjugated with DAB secondary antibody (for detecting PD-L1) or AP secondary antibody (for detecting PD-1 and CD8) to detect staining results. After the detection, the tissue section is then counterstained by hematoxylin.

Figure 3:
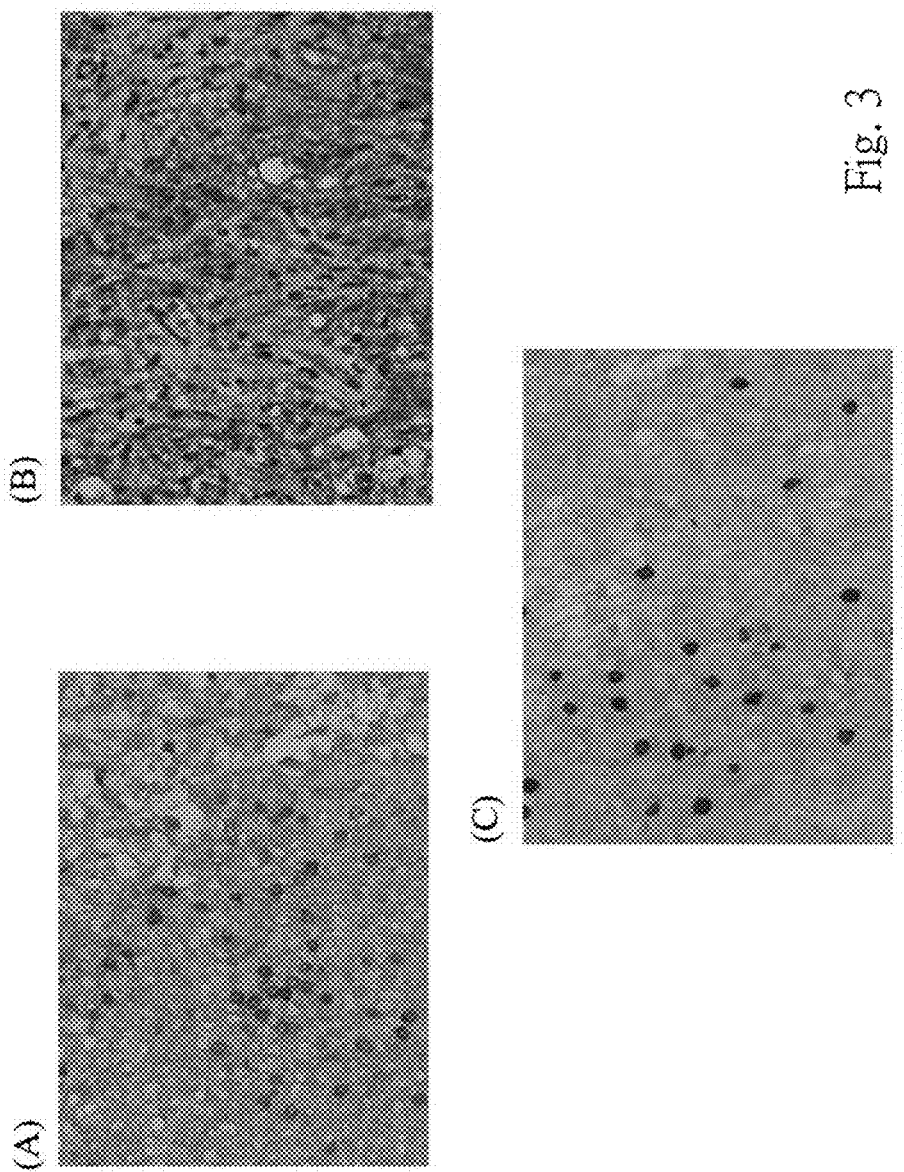
FIG. 3 is a set of micrographs of an immunohistochemistry, wherein (A) represents PD-1, (B) represents PD-L1, and (C) represents CD8.

FIG. 3 is a set of micrographs of an immunohistochemistry, wherein (A) represents the PD-1, (B) represents the PD-L1, and (C) represents the CD8. A magnification of the micrograph is 400×. In FIG. 3, nuclei present blue, parts expressed the PD-L1 present dark brown, and parts expressed the PD-1 and the CD8 present red in stained brain tissue sections of the GBM patients.

2. The Sample is the Blood

The sample in this example is the blood, which is drawing from the GBM patient. The blood is made as a cell block, and then is performed the immunohistochemistry to detect the expression levels of the biomarkers of the PD-1 and the CD8.

The cell block is performed as follows steps. The blood from the patient is placed in microcentrifuge tubes and fixed in formalin for 1 hour at room temperature. Then, the material is centrifuged for 30 seconds at 15,000 rpm and the supernatant is carefully discarded by pipetting, leaving a formalin-fixed cell pellet. The formalin-fixed cell pellet is resuspended with a minimal volume of 3% (w/v) ultra-low gelling temperature agarose solution at room temperature and centrifuged for 30 seconds at 15,000 rpm. The supernatant is carefully discarded by pipetting and the resulting agarose cell suspension is allowed to solidify for 10 to 20 minutes at −20° C. Each of the solidified agarose cell buttons is transferred into the cap of the microcentrifuge tube. Then, the cap with an agarose cell button at the bottom is filled with 3% standard agarose solution. The resulting agarose gel disk is removed from the cap and then subjected to tissue processing for paraffin embedding to obtain the cell block.

The cell block is further performed the immunohistochemistry. Primary antibodies used in the immunohistochemistry are PD-1 (Leica) and CD8 (Leica), and a dilution is 1:200 and 1:100 respectively. The cell block is retrieved by EDTA buffer solution at 100° C. for 20 minutes, and then hybridized with the primary antibody at room temperature for 1 hour. The cell block is conjugated with AP secondary antibody to detect staining results. After the detection, the cell block is then counterstained by hematoxylin.

III. Result Analysis of the Tumor Tissue Sample

1. Diagnosis of the Tissue Section of the GBM Patient

A histopathological diagnosis of the GBM is typically based on a tissue pattern rather than on an identification of certain cell types. The presence of highly anaplastic glial cells, mitotic activity and vascular proliferation and/or necrosis is required. For this purpose, six different cell types are defined: small anaplastic cell (SAC), small fibrillated cell (SFC), fibrillated astrocyte (FA), pleomorphic astrocyte (PA), gemistocytic astrocyte (GA), and large bizarre cell (LBC). In addition, two PD-L1 staining patterns, fibrillary staining pattern (fibrillary) and membranous staining pattern (membranous), are observed in immunohistochemistry stained tissue sections.

Table 2 shows diagnosis results of the immunohistochemistry stained tissue sections in 35 GBM patients of this clinical trial program. A pathologist analyzes the immunohistochemistry stained tissue sections without knowing the diagnostic results during the histopathological diagnosis. In Table 2, 35 patients participating in this clinical trial program are all indeed the GBM patients.

TABLE 2

The diagnosis results of the GBM patients

| ID | Cytologic Composition | Staining Pattern |
|---|---|---|
| 1 | FA | Fibrillary |
| 2 | FA | Fibrillary |
| 3 | PA | Membranous |
| 4 | FA | Fibrillary |
| 5 | FA | Fibrillary |
| 6 | PA | Fibrillary |
| 7 | PA | Membranous |
| 8 | SFC | Fibrillary |
| 9 | SFC | Fibrillary |
| 10 | LBC | Fibrillary |
| 11 | FA | Fibrillary |
| 12 | SAC | Membranous |
| 13 | FA | Fibrillary |
| 14 | PA | Membranous |
| 15 | FA | Fibrillary |
| 16 | PA | Membranous |
| 17 | FA | Membranous |
| 18 | PA | Fibrillary |
| 19 | FA | Fibrillary |
| 20 | SFC | Fibrillary |
| 21 | GA | Fibrillary |
| 22 | PA | Fibrillary |
| 23 | FA | Fibrillary |
| 24 | PA | Fibrillary |
| 25 | FA | Fibrillary |
| 26 | PA | Fibrillary |
| 27 | LBC | Membranous |
| 28 | SFC | Fibrillary |
| 29 | FA | Fibrillary |
| 30 | SFC | Membranous |
| 31 | FA | Fibrillary |
| 32 | GA | Fibrillary |
| 33 | FA | Membranous |
| 34 | PA | Fibrillary |
| 35 | PA | Fibrillary |

2. Semi-Quantitative Analysis

The diagnosis results of the immunohistochemistry stained tissue sections in 35 GBM patients are further performed semi-quantitative analysis by the H-score method or the image processing method.

2.1 H-Score Method

2.1.1 PD-L1

In the H-score method, the PD-L1 expression level is analyzed by estimating a staining intensity of the PD-L1 on the cell membrane of the GBM in 25 high power fields (magnification 400×), and it is classified as 0, 1, and 2. Criteria of the classification are as follows: 0 represents that no GBM cells are stained with color, 1 represents that the GBM cells are stained with weak or moderate intensity of color on intact cell membrane or in cytoplasm, and 2 represents that the GBM cells are stained with strong intensity of color on intact cell membrane or in cytoplasm. The stained GBM cell number is estimated as a percentage (stained cell number/total cell number×100%), and the signal value (HSCORE) in the H-score method is calculated according to the following formula I:

$$HSCORE=\Sigma(i \times Pi) \qquad \text{formula I}$$

where i represent the staining intensity of the biomarker (0, 1, or 2), and Pi represent the percentage of the stained GBM cells (varied from 0% to 100%), wherein the signal value ranges from 0 to 200. The threshold is 80 in the H-score method for estimating the PD-L1 expression level. When the signal value calculated in the H-score method is greater than or equal to 80, it is defined as a high expression level of the PD-L1 (high PD-L1). When the signal value calculated in the H-score method is less than 80, it is defined as a low expression level of the PD-L1 (low PD-L1).

2.1.2 PD-1 and CD8

In the H-score method, the PD-1 expression level and CD8 expression level are analyzed by counting the stained cell number in 25 high power fields (magnification 400×), and the counted cell number in 25 high power fields are then summed up to obtain the signal value. After the calculation of the immunohistochemistry stained tissue sections in all GBM patients treated with the immunotherapy is based on the dendritic cell tumor vaccine (n=21), a median can be calculated. The threshold is the median in the H-score method for estimating the PD-1 expression level and the CD8 expression level. When the signal value calculated in the H-score method is greater than or equal to the median, it is defined as the high expression level of the biomarker. When the signal value calculated in the H-score method is less than the median, it is defined as the low expression level of the biomarker.

Table 3 shows statistics data in the H-score method, wherein analyzed items are the cell numbers that expressed the PD-1 or the CD8 in the GBM patients treated with the immunotherapy treatment is based on the dendritic cell tumor vaccine, and the ratio of the expression level of the PD-1 to the expression level of the CD8 (the PD-1/CD8 ratio). The median for CD8, PD-1 and the PD-1/CD8 ratio is 231, 26, and 0.13, respectively. When the signal value calculated in the H-score method is greater than or equal to 231, it is defined as the high expression level of the CD8 (high CD8). When the signal value calculated in the H-score method is less than 231, it is defined as the low expression level of the CD8 (low CD8). When the signal value calculated in the H-score method is greater than or equal to 26, it is defined as the high expression level of the PD-1 (high PD-1). When the signal value calculated in the H-score method is less than 26, it is defined as the low expression level of the PD-1 (low PD-1). When the ratio of the signal value of the PD-1 to the signal value of the CD8 calculated in the H-score method is greater than or equal to 0.13, it is defined as a high PD-1/CD8 ratio. When the ratio of the signal value of the PD-1 to the signal value of the CD8 calculated in the H-score method is less than 0.13, it is defined as a low PD-1/CD8 ratio.

TABLE 3

| Biomarker | Mean | Median | Interquartile range | SD |
|---|---|---|---|---|
| CD8 | 358.00 | 231.00 | 177.00-532.00 | 271.66 |
| PD-1 | 84.52 | 26.00 | 8.50-125.00 | 120.00 |
| PD-1/CD8 | 0.24 | 0.13 | 0.03-0.42 | 0.24 |

2.2 Image Processing Method

Although the expression level of the PD-L1 can be analyzed by the H-score method, the H-score method is an artificial image quantitative analysis so that the definition of PD-L1 expression level is time-consuming or has some inaccuracies caused by an artificial interpretation. In addition, the intensity of the stained cells is difficult to quantify, it only depends on subjective artificial interpretation to determine the staining intensity. The expression level of the PD-L1 is also semi-quantitative analyzed by the image processing method in the present disclosure; hence the definitions of the high expression level of the PD-L1 and the low expression level of the PD-L1 are more objective.

A color space transformation using the RGB color model in this example to emphasize characteristics of required objects in color images. Firstly, micrographs are captured in 25 high power fields (magnification 400×). In the calculation of the staining intensity, the micrographs are converted from a red-green-blue digital to a red channel in order to obtain a RGB value. The threshold is 25,000 in the image processing method for estimating the PD-L1 expression level. When the RGB value calculated in the image processing method is greater than or equal to 25,000, it is defined as the high expression level of the PD-L1 (high PD-L1). When the RGB value calculated in the image processing method is less than 25,000, it is defined as the low expression level of the PD-L1 (low PD-L1). The RGB color model used in the image processing method is one embodiment of the present disclosure, but the present disclosure is not limited to this embodiment. The CMYK (cyan/magenta/yellow/key) color model or the HSI (hue/saturation/intensity) color model also can be used in the image processing method.

Figure 4:
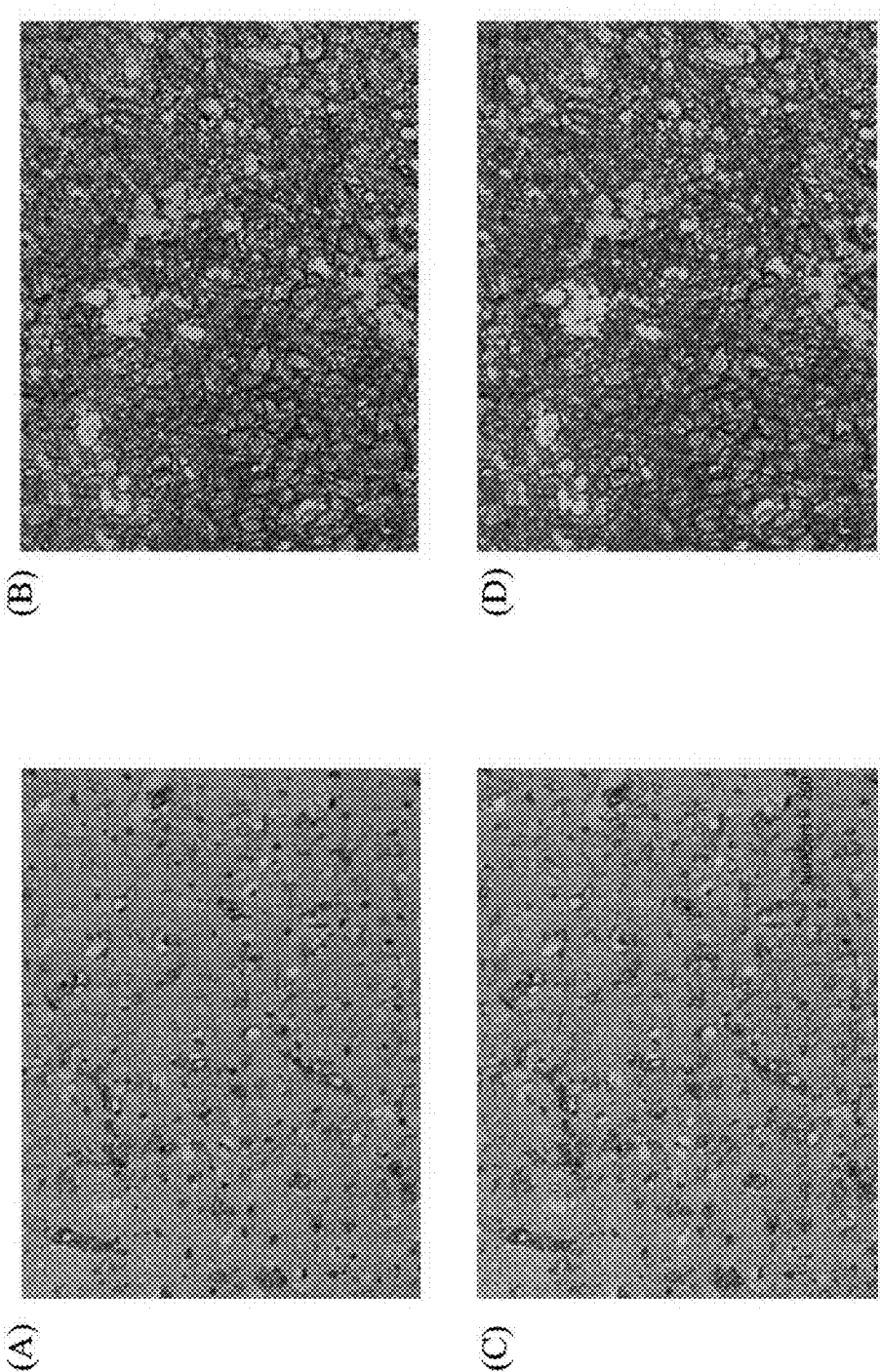
FIG. 4 is a set of micrographs showing expression levels of the PD-L1, wherein (A) is the micrograph showing a low expression level of the PD-L1 in a normal brain tissue, (B) is the micrograph showing a high expression level of the PD-L1 in a brain tissue of the GBM patient, (C) is a color-converted micrograph showing the low expression level of the PD-L1 in the normal brain tissue, and (D) is a color-converted micrograph showing the high expression level of the PD-L1 in the brain tissue of the GBM patient.

FIG. 4 is a set of micrographs showing expression levels of the PD-L1, wherein (A) is the micrograph showing the low expression level of the PD-L1 in a normal brain tissue, (B) is the micrograph showing a high expression level of the PD-L1 in a brain tissue of the GBM patient, (C) is a color-converted micrograph showing the low expression level of the PD-L1 in the normal brain tissue, and (D) is a color-converted micrograph showing the high expression level of the PD-L1 in the brain tissue of the GBM patient. The nuclei are marked as green crosses, which represents the cell number in the micrograph. Red part of the micrograph represents the expression of the PD-L1. In FIGS. 4(A) and 4(B), the calculated cell number is 260, and the RGB value is 3938 in the micrograph. Because the RGB value is less than 25,000, it is defined as the low expression level of the PD-L1 (low PD-L1). In FIGS. 4(C) and 4(D), the calculated cell number is 307, and the RGB value is 75347 in the micrograph. Because the RGB value is less than 25,000, it is defined as the high expression level of the PD-L1 (high PD-L1).

3. Statistical Analysis

3.1 Survival Analysis

35 GBM patients are classified into the high expression level of biomarker and the low expression level of the biomarker according to the semi-quantitative analysis. Statistical analysis is further performed by using GraphPad PRISM 4.05 (San Diego, Calif., USA) and SAS 9.01. A survival time is analyzed by Kaplan-Meier estimate, and a statistical significant of the survival time is further analyzed by a log rank test. A p-value of <0.05 is considered statistically significant in all statistical analysis of this example.

A survival analysis is a common statistical analysis of clinical trials in various cancers, and is a statistic that deals with time variable. In more details, the survival analysis deals with analysis of time duration until one or more events happen. Two evaluation indexes of the time variable, overall survival (OS) and disease free survival (DFS), are used in this example. The event is "death" in the evaluation index of the overall survival, and a length of time from a subject participating in the clinical trial until the death is then observed. The event is "tumor recurrence" in the evaluation index of the disease free survival, and the length of time from the subject participating in the clinical trial until the tumor recurrence is then observed.

Figure 5:
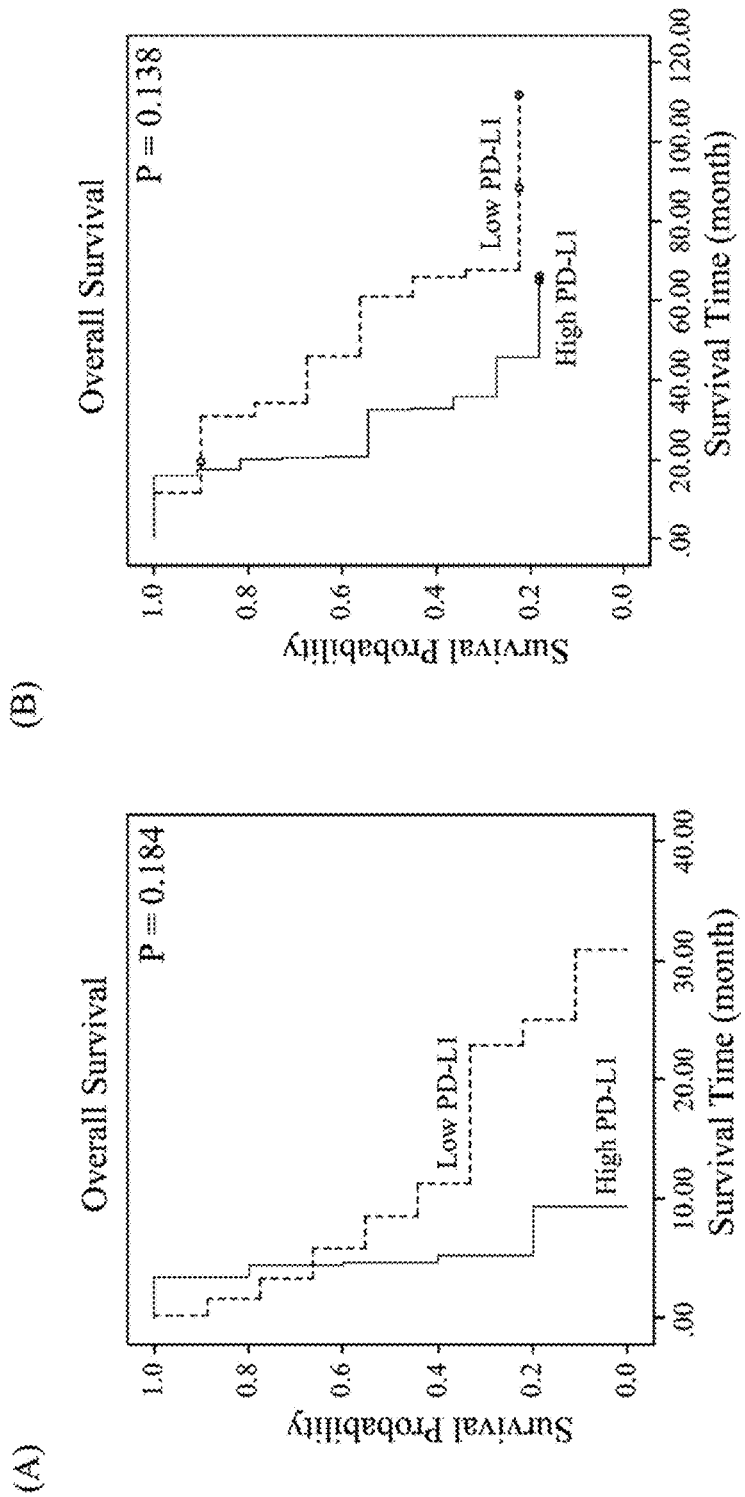
FIG. 5 is an overall survival curve of the GBM patients that are classified based on the expression level of the PD-L1, wherein (A) represents the overall survival curve of the GBM patients untreated with the dendritic cell tumor vaccine, (B) represents the overall survival curve of the GBM patients treated with the dendritic cell tumor vaccine.
Figure 6:
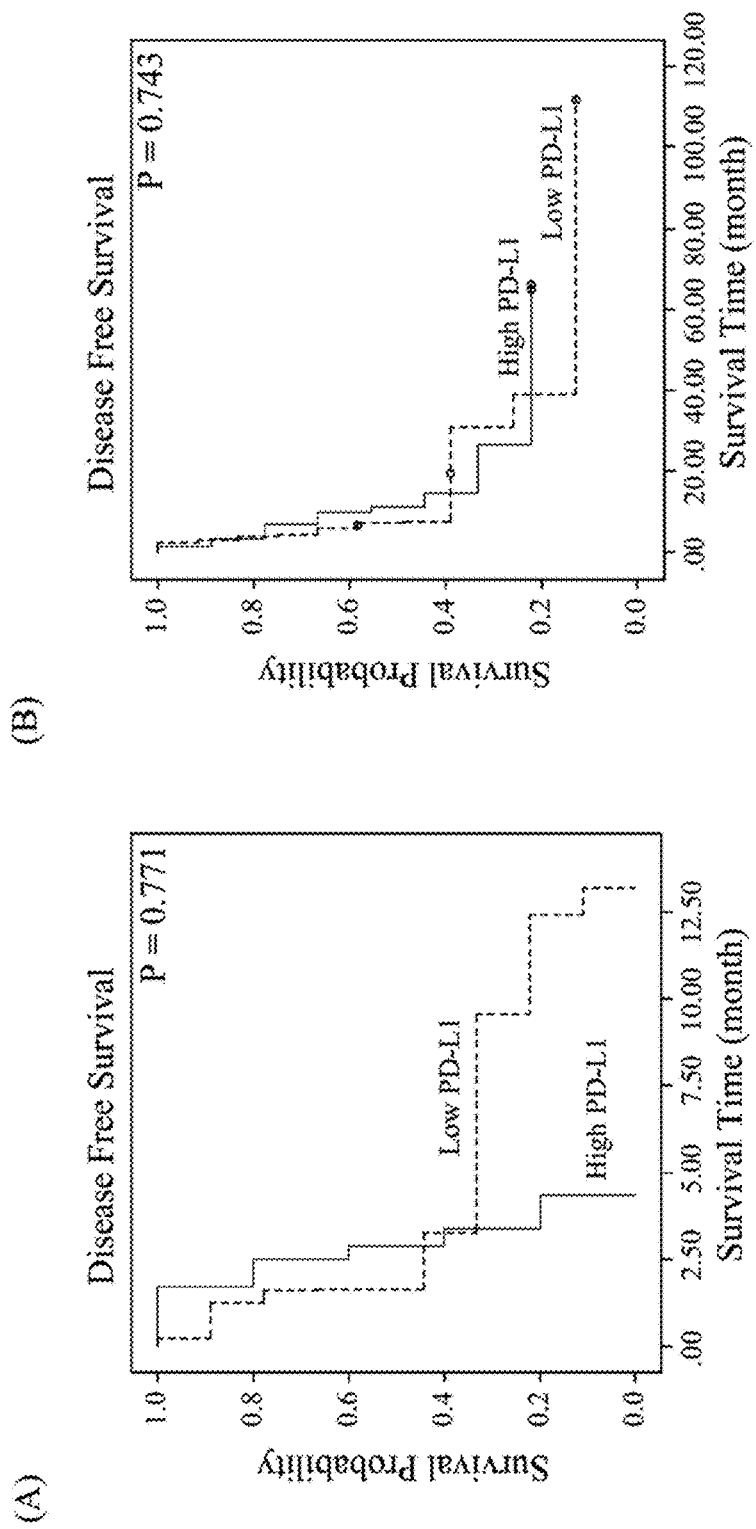
FIG. 6 is a disease free survival curve of the GBM patients that are classified based on the expression level of the PD-L1, wherein (A) represents the disease free survival curve of the GBM patients untreated with the dendritic cell tumor vaccine, (B) represents the disease free survival curve of the GBM patients treated with the dendritic cell tumor vaccine.
Figure 7:
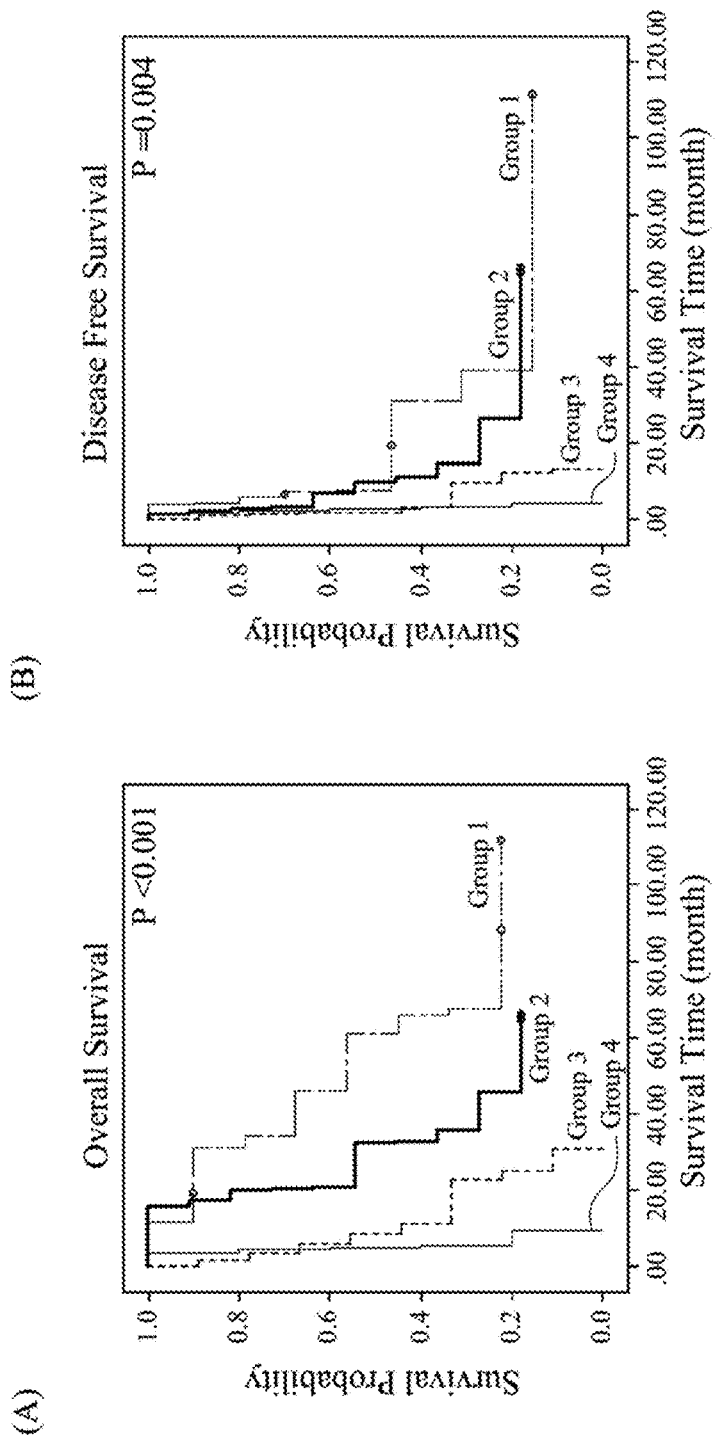
FIG. 7 is a set of survival curves of all GBM patients, wherein (A) represents the overall survival curve, (B) represents the disease free survival curve.
Figure 8:
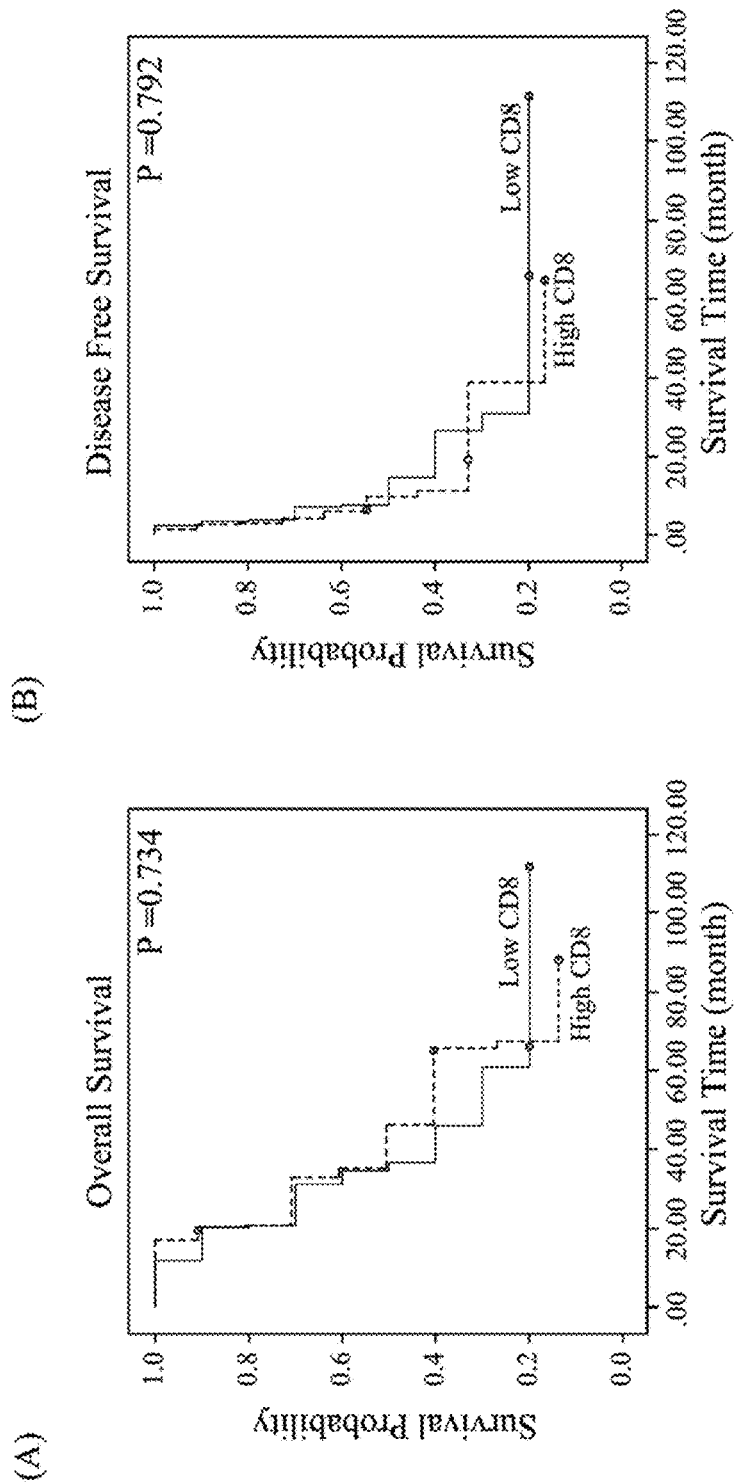
FIG. 8 is a set of the survival curves of the GBM patients treated with the dendritic cell tumor vaccine and further classified based on the expression level of the CD8, wherein (A) represents the overall survival curve, (B) represents the disease free survival curve.
Figure 9:
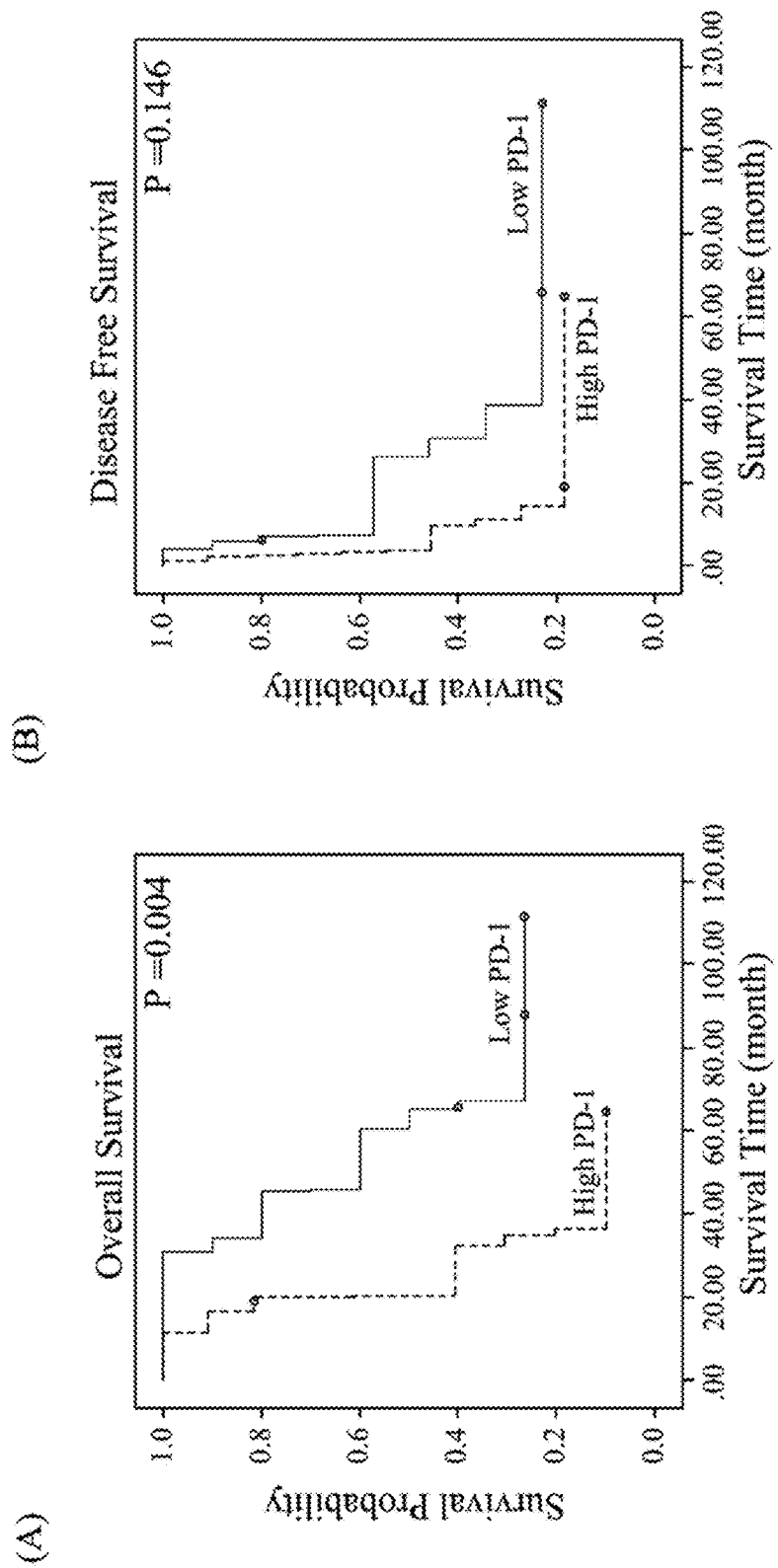
FIG. 9 is a set of the survival curves of the GBM patients treated with the dendritic cell tumor vaccine and further classified based on the expression level of the PD-1, wherein (A) represents the overall survival curve, (B) represents the disease free survival curve.
Figure 10:
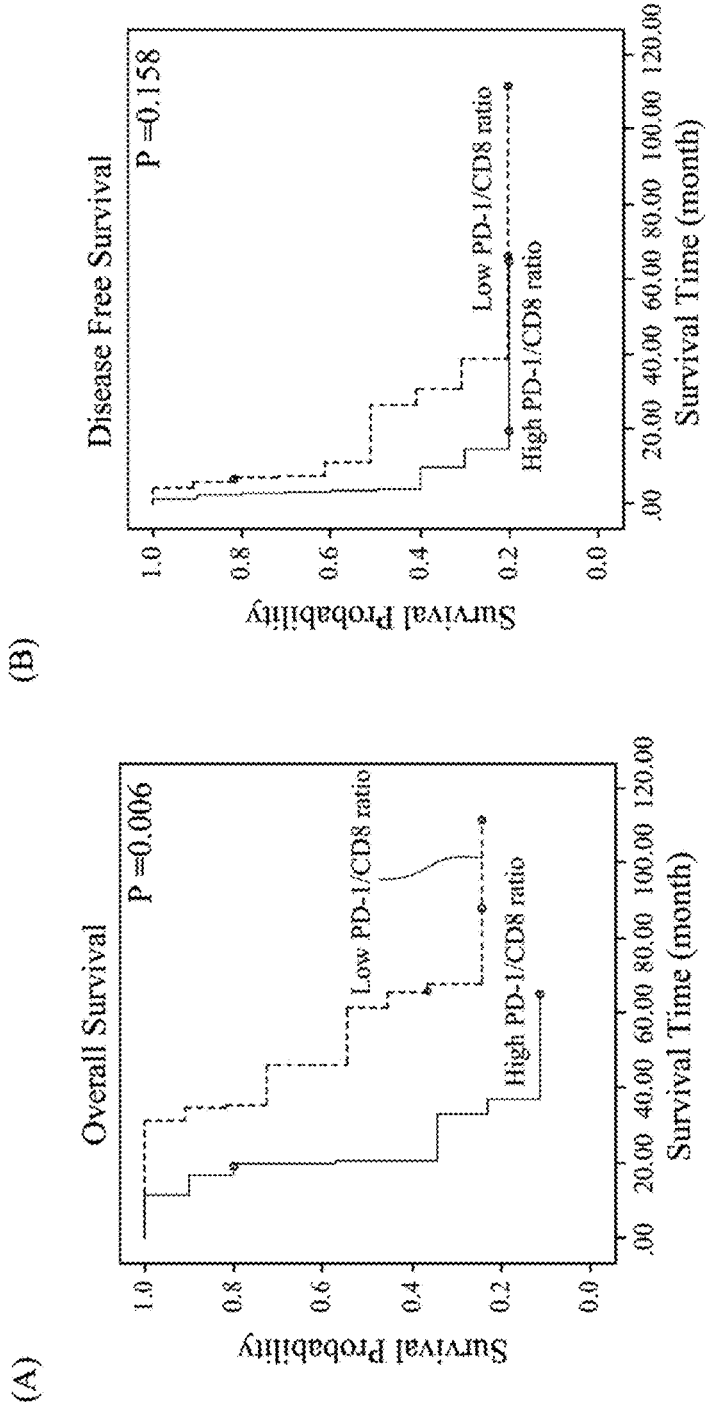
FIG. 10 is a set of the survival curves of the GBM patients treated with the dendritic cell tumor vaccine and further classified based on a ratio of the expression level of the PD-1 to the expression level of the CD8, wherein (A) represents the overall survival curve, (B) represents the disease free survival curve.
Figure 11:
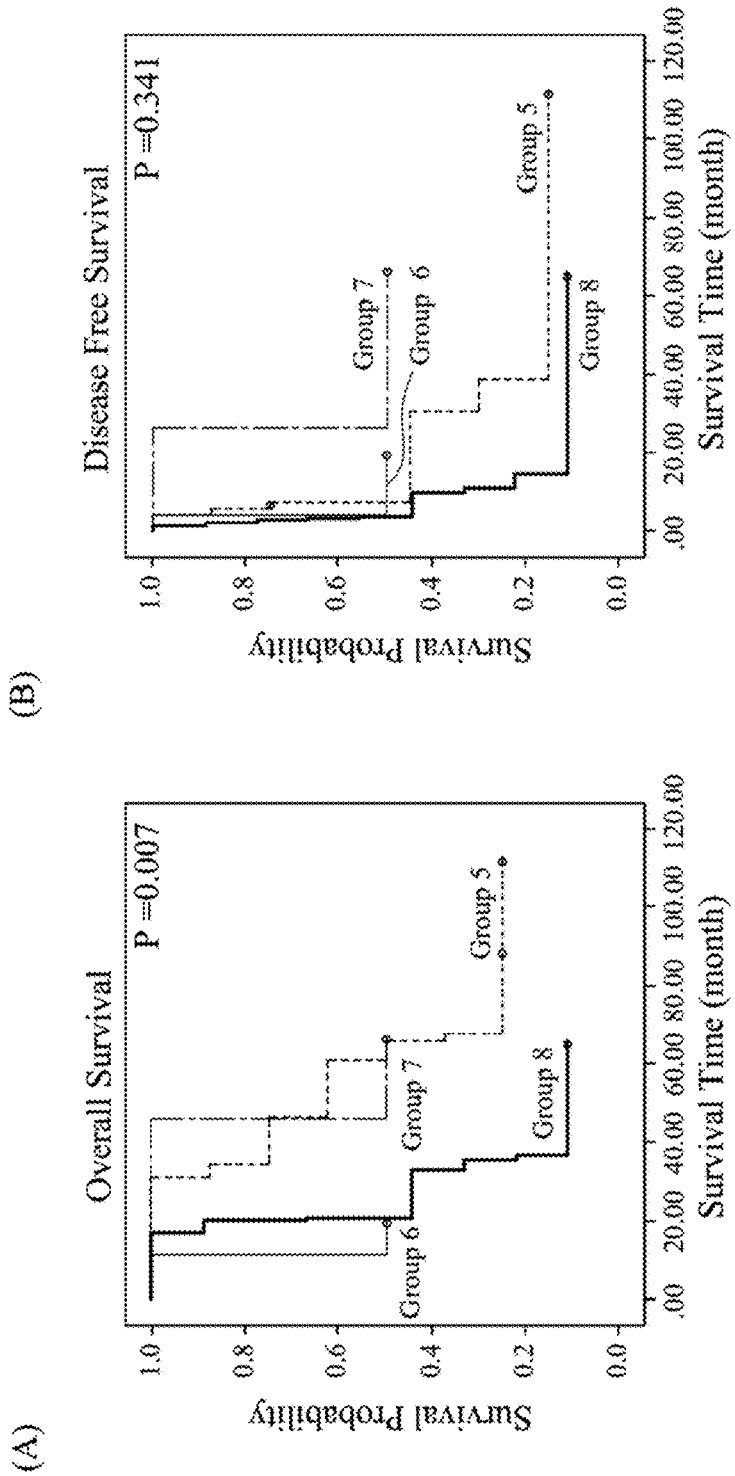
FIG. 11 is a set of the survival curves of the GBM patients treated with the dendritic cell tumor vaccine and further classified based on the expression level of the PD-1 and the expression level of the PD-L1, wherein (A) represents the overall survival curve, (B) represents the disease free survival curve.

FIG. 5 is an overall survival curve of the GBM patients that are classified based on the expression level of the PD-L1, wherein (A) represents the overall survival curve of the GBM patients untreated with the dendritic cell tumor vaccine, (B) represents the overall survival curve of the GBM patients treated with the dendritic cell tumor vaccine. FIG. 6 is a disease free survival curve of the GBM patients that are classified based on the expression level of the PD-L1, wherein (A) represents the disease free survival curve of the GBM patients untreated with the dendritic cell tumor vaccine, (B) represents the disease free survival curve of the GBM patients treated with the dendritic cell tumor vaccine. FIG. 7 is a set of survival curves of all GBM patients, wherein (A) represents the overall survival curve, (B) represents the disease free survival curve. FIG. 8 is a set of the survival curves of the GBM patients treated with the dendritic cell tumor vaccine and further classified based on the expression level of the CD8, wherein (A) represents the overall survival curve, (B) represents the disease free survival curve. FIG. 9 is a set of the survival curves of the GBM patients treated with the dendritic cell tumor vaccine and further classified based on the expression level of the PD-1, wherein (A) represents the overall survival curve, (B) represents the disease free survival curve. FIG. 10 is a set of the survival curves of the GBM patients treated with the dendritic cell tumor vaccine and further classified based on a ratio of the expression level of the PD-1 to the expression level of the CD8, wherein (A) represents the overall survival curve, (B) represents the disease free survival curve. FIG. 11 is a set of the survival curves of the GBM patients treated with the dendritic cell tumor vaccine and further classified based on the expression level of the PD-1 and the expression level of the PD-L1, wherein (A) represents the overall survival curve, (B) represents the disease free survival curve. There are 35 GBM patients in this example, wherein 14 GBM patients are untreated with the dendritic cell tumor vaccine, and 21 GBM patients are treated with the dendritic cell tumor vaccine. A hollow dot in the figure represents a time point in an occurrence of censored data.

In FIG. 5, an overall survival time in the GBM patient who has the low expression level of the PD-L1 is longer than that in the GBM patient who has the high expression level of the PD-L1 regardless of the GBM patient treated with or without the dendritic cell tumor vaccine. The p-value analyzed by the log rank test is 0.184 between the low expression level of the PD-L1 and the high expression level of the PD-L1 in the GBM patients untreated with the dendritic cell tumor vaccine. The p-value is 0.138 between the low expression level of the PD-L1 and the high expression level of the PD-L1 in the GBM patients treated with the dendritic cell tumor vaccine.

In FIG. 6, the time of the tumor recurrence in the GBM patient who has the low expression level of the PD-L1 is longer than that in the GBM patient who has the high expression level of the PD-L1 regardless of the GBM patient treated with or without the dendritic cell tumor vaccine. The p-value analyzed by the log rank test is 0.771 between the low expression level of the PD-L1 and the high expression level of the PD-L1 in the GBM patients untreated with the dendritic cell tumor vaccine. The p-value is 0.743 between the low expression level of the PD-L1 and the high expression level of the PD-L1 in the GBM patients treated with the dendritic cell tumor vaccine.

There are four groups in FIG. 7. In a group 1, the GBM patient has the low expression of the PD-L1 and is treated with the dendritic cell tumor vaccine. In a group 2, the GBM patient has the high expression of the PD-L1 and is treated with the dendritic cell tumor vaccine. In a group 3, the GBM patient has the low expression of the PD-L1 and is untreated with the dendritic cell tumor vaccine. In a group 4, the GBM patient has the high expression of the PD-L1 and is untreated with the dendritic cell tumor vaccine. In FIG. 7(A), the overall survival in the GBM patient treated with the dendritic cell tumor vaccine (the group 1 and the group 2) is longer than that in the GBM patient untreated with the dendritic cell tumor vaccine (the group 3 and the group 4). In addition, the overall survival in the GBM patient who has the low expression level of the PD-L1 is longer than that in the GBM patient who has the high expression level of the PD-L1 regardless of the GBM patient treated with or without the dendritic cell tumor vaccine. The p-value analyzed by the log rank test are as follows: the p-value is less than 0.001 among four groups, the p-value is less than 0.001 between the group 3 and the group 1, the p-value is less than 0.001 between the group 4 and the group 2, and the p-value is less than 0.001 between the group 3 and the group 2.

In FIG. 7(B), a disease free survival time in the GBM patient treated with the dendritic cell tumor vaccine (the group 1 and the group 2) is longer than that in the GBM patient untreated with the dendritic cell tumor vaccine (the group 3 and the group 4). In addition, the disease free survival time in the GBM patient who has the low expression level of the PD-L1 is longer than that in the GBM patient who has the high expression level of the PD-L1 regardless of the GBM patient treated with or without the dendritic cell tumor vaccine. The p-value analyzed by the log rank test are as follows: the p-value is 0.004 among four groups, the p-value is 0.016 between the group 3 and the group 1, the p-value is 0.020 between the group 4 and the group 2, and the p-value is 0.048 between the group 3 and the group 2.

In FIG. 8, there are no differences in the overall survival time and the disease free survival time between the GBM patient who has the low expression level of the CD8 and the GBM patient who has the high expression level of the CD8, wherein the GBM patient is treated with the dendritic cell tumor vaccine. The p-value is 0.734 between the low expression level of the CD8 and the high expression level of the CD8 in the overall survival time, and the p-value is 0.792 between the low expression level of the CD8 and the high expression level of the CD8 in disease free survival time.

In FIG. 9, there is a significant difference (p=0.004) in the overall survival time between the GBM patient who has the low expression level of the PD-1 and the GBM patient who has the high expression level of the PD-1, wherein the GBM patient is treated with the dendritic cell tumor vaccine. There is also the difference (p=0.146) in the disease free survival time between the low expression level of the PD-1 and the high expression level of the PD-1 in the GBM patient treated with the dendritic cell tumor vaccine.

In FIG. 10, when a analysis criteria is the ratio of the expression level of the PD-1 to the expression level of the CD8 (the PD-1/CD8 ratio), the overall survival time in the GBM patient who has the low PD-1/CD8 ratio is longer than that in the GBM patient who has the high PD-1/CD8 ratio, wherein the GBM patient is treated with the dendritic cell tumor vaccine. The p-value is 0.006. The disease free survival time in the GBM patient who has the low PD-1/CD8 ratio is also longer than that in the GBM patient who has the high PD-1/CD8 ratio. The p-value is 0.158.

To discuss the effect of the expression level of the PD-1 and the expression level of the PD-L1 on the overall survival time and the disease free survival time of the GBM patients treated with the dendritic cell tumor vaccine. There are four groups in FIG. 11. In a group 5, the GBM patient has the low expression of the PD-1 and the low expression of the PD-L1. In a group 6, the GBM patient has the high expression of the PD-1 and the low expression of the PD-L1. In a group 7, the GBM patient has the low expression of the PD-L1 and the high expression of the PD-L1. In a group 8, the GBM patient has the high expression of the PD-1 and the high expression of the PD-L1. In FIG. 11(A), the group has the longest overall survival time is the GBM patient who has the low expression of the PD-1 and the low expression of the PD-L1 (group 5). In view of the expression level of the PD-1, the overall survival time in the GBM patients who has the low expression level of the PD-1 (group 5 and group 7) is longer than that in the GBM patients who has the high expression level of the PD-1 (group 6 and group 8). However, in view of the expression level of the PD-L1, the overall survival time in the GBM patients who has the high expression of the PD-1 and the low expression of the PD-L1 (group 6) is shorter than that in the GBM patients who has the low expression of the PD-L1 and the high expression of the PD-L1 (group 7). It indicates that the expression level of the PD-1 is more important than the expression level of the PD-L1 in the GBM patient treated with the dendritic cell tumor vaccine. The p-value analyzed by the log rank test are as follows: the p-value is 0.007 among four groups, the p-value is 0.046 between the group 5 and the group 6, the p-value is 0.851 between the group 5 and the group 7, the p-value is 0.018 between the group 5 and the group 8, the p-value is 0.317 between the group 6 and the group 7, the p-value is 0.142 between the group 6 and the group 8, and the p-value is 0.129 between the group 7 and the group 8.

In FIG. 11(B), the group has the longest disease free survival time is the GBM patient who has the low expression of the PD-1 and the low expression of the PD-L1 (group 5). The differences among four groups are not significant in the disease free survival analysis. Although the disease free survival time in the GBM patients who has the low expression level of the PD-1 (group 5 and group 7) is longer than that in the GBM patients who has the high expression level of the PD-1 (group 6 and group 8), the differences are insignificant. The p-value analyzed by the log rank test are as follows: the p-value is 0.341 among four groups, the p-value is 0.809 between the group 5 and the group 6, the p-value is 0.388 between the group 5 and the group 7, the p-value is 0.274 between the group 5 and the group 8, the p-value is 0.317 between the group 6 and the group 7, the p-value is 0.330 between the group 6 and the group 8, and the p-value is 0.129 between the group 7 and the group 8.

The results of the survival analysis indicate that both the overall survival time and the disease free survival time in the GBM patient who has the low expression level of the PD-L1 are longer than those in the GBM patient who has the high expression level of the PD-L1 regardless of the GBM patient treated with or without the dendritic cell tumor vaccine. In particular, the difference is more significant in the GBM patient treated with the dendritic cell tumor vaccine. It indicates that the GBM patient who has the low expression level of the PD-L1 is applicable to be treated with the immunotherapy treatment based on the dendritic cell tumor vaccine, and has a better prognosis after the treatment. In addition, the overall survival time and the disease free survival time in the GBM patient who has the low expression level of the PD-1 are longer than those in the GBM patient who has the high expression level of the PD-1, wherein the GBM patient is treated with the dendritic cell tumor vaccine. The overall survival time and the disease free survival time in the GBM patient who has the low PD-1/CD8 ratio are longer than those in the GBM patient who has the high PD-1/CD8 ratio, wherein the GBM patient is treated with the dendritic cell tumor vaccine. The results suggest that the GBM patient who has the low expression level of the PD-1 or the low PD-1/CD8 ratio is applicable to be treated with the immunotherapy treatment based on dendritic cell tumor vaccine, and has a better prognosis after the treatment, especially the immunotherapy based on dendritic cell tumor vaccine.

3.2 Treatment Effect Assessment Analysis

The log rank test is only used to determine whether the differences are significant between different groups, but it can not estimate a treatment effect. Therefore, a Cox proportional hazard model is used for estimating the treatment effect in this example.

Table 4 shows a hazard ratio (HR) and a 95% confidence interval (CI) in the GBM patient treated with the dendritic cell tumor vaccine. When the hazard ratio is greater than 1, it indicates that the percentage of a death occurrence in the patient expressing the biomarker is greater than that in the patient who does not express the biomarker. Furthermore, when the HR is greater than 1, the p-value is less than 0.05 and the 95% CI is less than 1, it indicates that the biomarker has a statistically significant difference. In Table 4, the effect of the PD-1 on the overall survival time has the statistical significant. The percentage of the death occurrence in the GBM patient who has the high expression level of the PD-1 is 4.72 times higher than that in the GBM patient who has the low expression level of the PD-1. The result suggests that the PD-1 is an essential affect factor on the overall survival time in the GBM patient treated with the dendritic cell tumor vaccine.

TABLE 4

| Variable | Overall survival time | | | Disease-free survival time | | |
|---|---|---|---|---|---|---|
| | P-value | HR | 95% CI | P-value | HR | 95% CI |
| PD-1 | 0.008* | 4.720 | 1.495-14.898 | 0.154 | 2.095 | 0.759-5.784 |
| PD-L1 | 0.165 | 2.120 | 0.733-6.127 | 0.501 | 1.408 | 0.520-3.808 |
| CD8 | 0.735 | 0.843 | 0.315-2.259 | 0.792 | 1.142 | 0.426-3.062 |

3.3 Correlation Coefficient Analysis

A Pearson correlation coefficient is used in this example to analyze a correlation between the expression level of the PD-1 and the overall survival time, the correlation between the expression level of the PD-1 and the disease free survival time, the correlation between the PD-1/CD8 ratio and the overall survival time, and the correlation between the PD-1/CD8 ratio and the disease free survival time in the GBM patient treated with the dendritic cell tumor vaccine. The Pearson correlation coefficient is used to analyze a strength of a linear correlation between two consecutive variables (x, y), and the calculated Pearson correlation coefficient (r) ranges from −1 to +1. When the r is greater than 0, there is a positive correlation between the two variables. That is, when as the x increases, the y also increases and vice versa. When the r is less than 0, there is a negative correlation between the two variables. That is, when as the x increases, the y decreases and vice versa. A degree of the correlation between two variables is depended upon |r|, where 1 is a total correlation, 0.7-0.99 is a high correlation, 0.4-0.69 is a moderate correlation, 0.1-0.39 is a low correlation, 0.01-0.09 is near no correlation, and 0 is no correlation.

Figure 12:
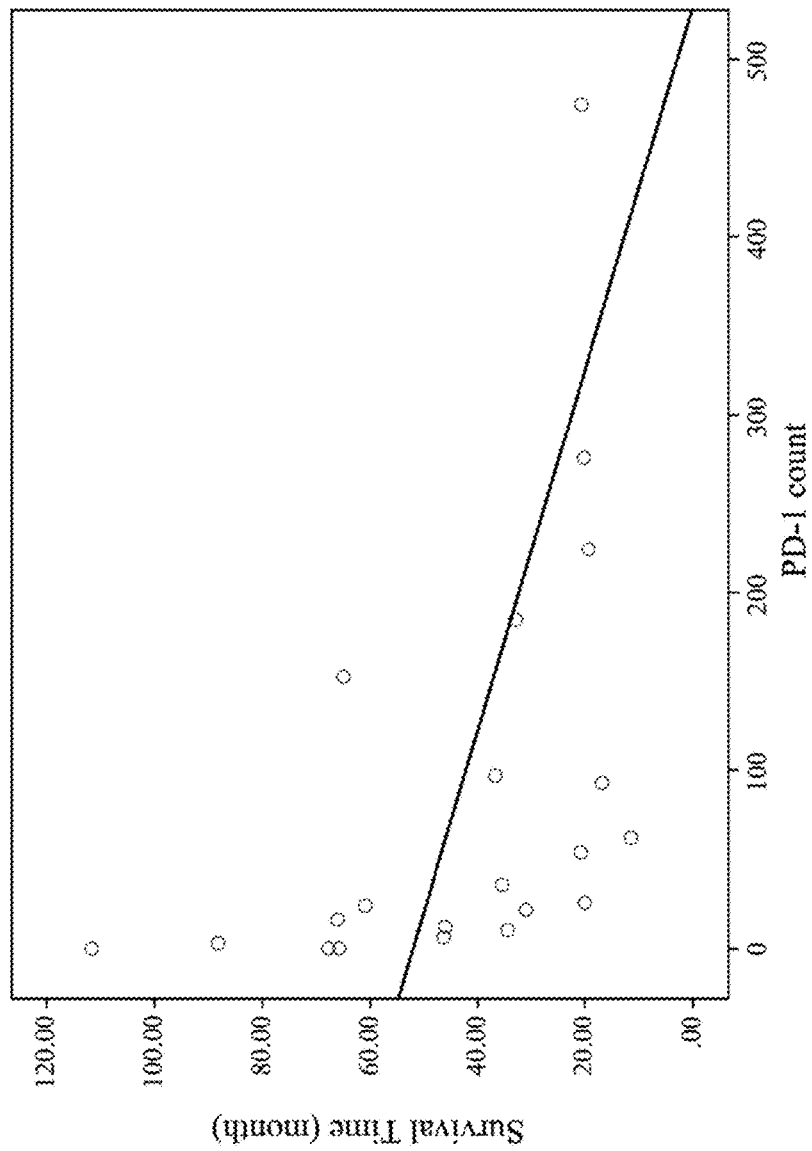
FIG. 12 is a correlation diagram between the PD-1 and an overall survival time.
Figure 13:
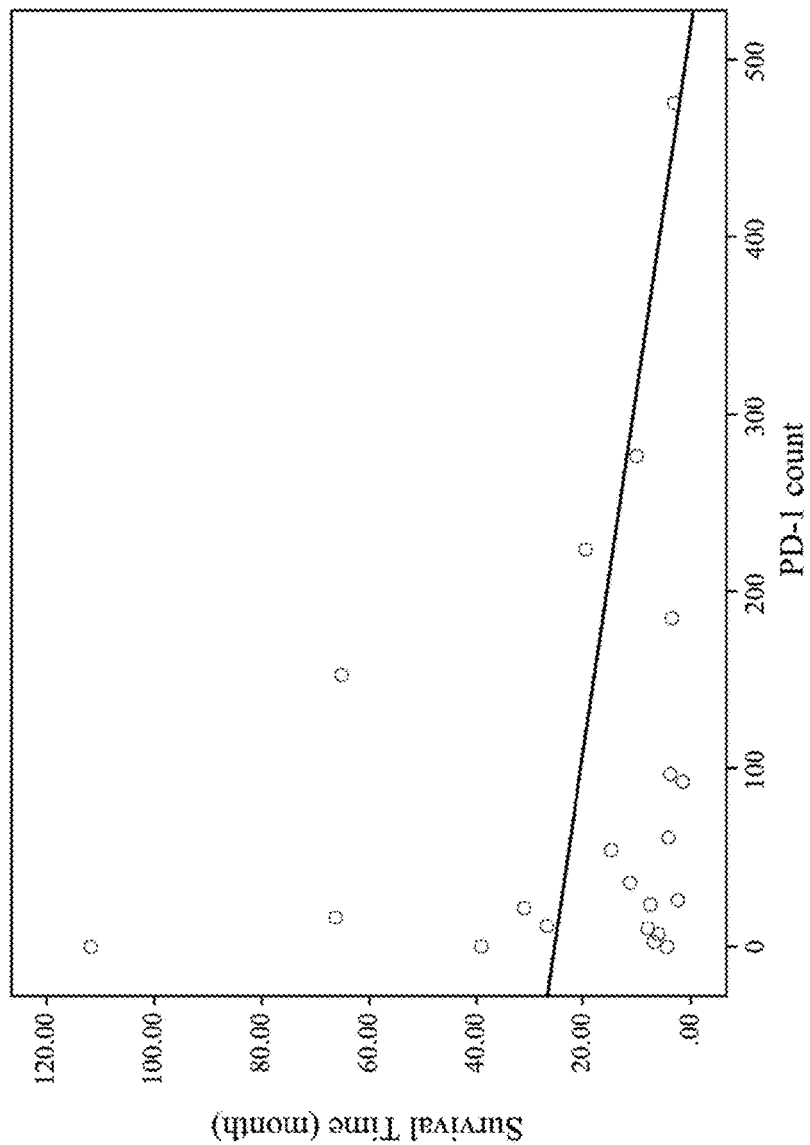
FIG. 13 is a correlation diagram between the PD-1 and a disease free survival time.
Figure 14:
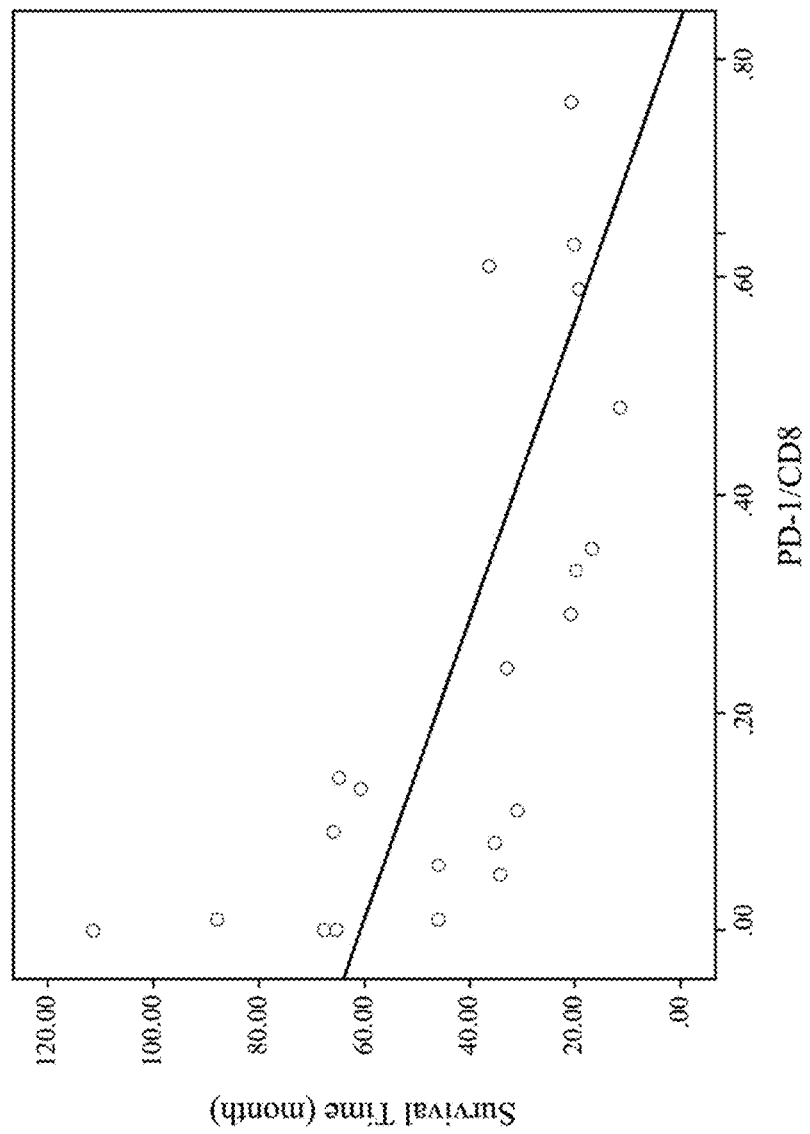
FIG. 14 is a correlation diagram between the ratio of the expression level of the PD-1 to the expression level of the CD8 and the overall survival time.
Figure 15:
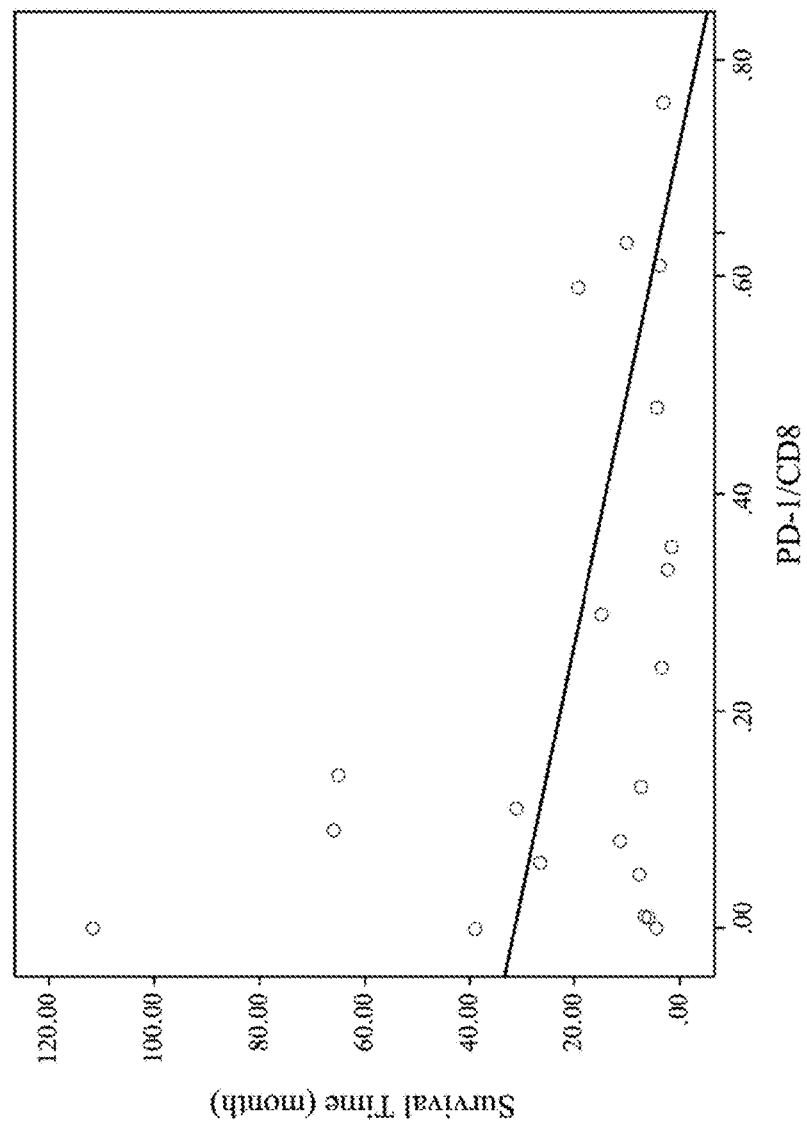
FIG. 15 is a correlation diagram between the ratio of the expression level of the PD-1 to the expression level of the CD8 and the disease free survival time.

FIG. 12 is a correlation diagram between the PD-1 and an overall survival time. A correlation coefficient between the PD-1 and the overall survival time is shown in Table 5 as follows. FIG. 13 is the correlation diagram between the PD-1 and a disease free survival time. The correlation coefficient between the PD-1 and the disease free survival time is shown in Table 6 as follows. FIG. 14 is the correlation diagram between the ratio of the expression level of the PD-1 to the expression level of the CD8 and the overall survival time. The correlation coefficient between the ratio of the expression level of the PD-1 to the expression level of the CD8 and the overall survival time is shown in Table 7 as follows. FIG. 15 is the correlation diagram between the ratio of the expression level of the PD-1 to the expression level of the CD8 and the disease free survival time. The correlation coefficient between the ratio of the expression level of the PD-1 to the expression level of the CD8 and the disease free survival time is shown in Table 8 as follows.

TABLE 5

| | | Disease Free Survival (month) | PD-1 Count |
|---|---|---|---|
| Overall Survival (month) | Pearson Correlation | 1 | −0.446* |
| | Sig. (two-tailed) | — | 0.042 |
| | number | 21 | 21 |
| PD-1 Count | Pearson Correlation | −0.446* | 1 |
| | Sig. (two-tailed) | 0.042 | — |
| | number | 21 | 21 |

TABLE 6

| | | Disease Free Survival (month) | PD-1 Count |
|---|---|---|---|
| Overall Survival (month) | Pearson Correlation | 1 | −0.338 |
| | Sig. (two-tailed) | — | 0.067 |
| | number | 21 | 21 |
| PD-1 Count | Pearson Correlation | −0.338 | 1 |
| | Sig. (two-tailed) | 0.067 | — |
| | number | 21 | 21 |

TABLE 7

| | | Overall Survival (month) | PD-1/CD8 |
|---|---|---|---|
| Disease Free Survival (month) | Pearson Correlation | 1 | −0.677** |
| | Sig. (two-tailed) | — | 0.001 |
| | number | 21 | 21 |
| PD-1/CD8 | Pearson Correlation | −0.677** | 1 |
| | Sig. (two-tailed) | 0.001 | — |
| | number | 21 | 21 |

TABLE 8

| | | Disease Free Survival (month) | PD-1/CD8 |
|---|---|---|---|
| Disease Free Survival (month) | Pearson Correlation | 1 | −0.377 |
| | Sig. (two-tailed) | — | 0.092 |
| | number | 21 | 21 |
| PD-1/CD8 | Pearson Correlation | −0.377 | 1 |
| | Sig. (two-tailed) | 0.092 | — |
| | number | 21 | 21 |

In FIG. 12 and Table 5, there is the negative correlation between the expression level of the PD-1 and the overall survival time. The Pearson correlation coefficient is −0.446; it indicates that there is a statistically significant correlation between the expression level of the PD-1 and the overall survival time. In FIG. 13 and Table 6, there is the negative correlation between the expression level of the PD-1 and the disease free survival time. The Pearson correlation coefficient is −0.338; it indicates that there is the low correlation between the expression level of the PD-1 and the disease survival time. In FIG. 14 and Table 7, there is the negative correlation between the PD-1/CD8 ratio and the overall survival time. The Pearson correlation coefficient is −0.677; it indicates that there is the statistically significant correlation between the PD-1/CD8 ratio and the overall survival time. In FIG. 15 and Table 8, there is the negative correlation between the PD-1/CD8 ratio and the disease free survival time. The Pearson correlation coefficient is −0.377; it indicates that there is the low correlation between the PD-1/CD8 ratio and the disease survival time.

The results of the correlation coefficient analysis suggest that the overall survival time and disease free survival time are longer when the expression level of the PD-1 is lower in the GBM patients treated with the dendritic cell tumor vaccine. In addition, the overall survival time and disease free survival time are longer when the PD-1/CD8 ratio is lower in the GBM patients treated with the dendritic cell tumor vaccine. It means that the GBM patient who has the low expression level of the PD-1 or the low PD-1/CD8 ratio is applicable to be treated with the immunotherapy treatment based on dendritic cell tumor vaccine, and has the better prognosis after the treatment, especially the immunotherapy based on dendritic cell tumor vaccine.

4. Result Analysis of the Blood Sample

4.1 Correlation Coefficient Analysis

Table 9 shows immunohistochemistry stained cell block results analyzed by the H-score method in 13 GBM patients treated with the dendritic cell tumor vaccine, wherein the analyzed items are the cell numbers that expressed the PD-1 or the CD8 in peripheral blood mononuclear cells (PBMC) of the GBM patients treated with the immunotherapy treatment is based on the dendritic cell tumor vaccine and the tumor infiltrating lymphocytes (TIL) of the GBM patients treated with the immunotherapy treatment is based on the dendritic cell tumor vaccine, and the ratio of the expression level of the PD-1 to the expression level of the CD8 (PD-1/CD8 ratio).

In the H-score method, the PD-1 expression level and CD8 expression level are analyzed by counting the stained cell number in 25 high power fields (magnification 400×), and the counted cell number in 25 high power fields are then summed up to obtain the signal value. After the calculation of the immunohistochemistry stained cell block in the GBM patients treated with the immunotherapy is based on the dendritic cell tumor vaccine (n=13), a median can be calculated. The threshold is the median in the H-score method for estimating the PD-1 expression level and the CD8 expression level. When the signal value calculated in the H-score method is greater than or equal to the median, it is defined as the high expression level of the biomarker. When the signal value calculated in the H-score method is less than the median, it is defined as the low expression level of the biomarker. The median for CD8, PD-1 and the PD-1/CD8 ratio is 231, 26, and 0.13, respectively. When the signal value calculated in the H-score method is greater than or equal to 231, it is defined as the high CD8. When the signal value calculated in the H-score method is less than 231, it is defined as the low CD8. When the signal value calculated in the H-score method is greater than or equal to 26, it is defined as the high PD-1. When the signal value calculated in the H-score method is less than 26, it is defined as the low PD-1. When the ratio of the signal value of the PD-1 to the signal value of the CD8 calculated in the H-score method is greater than or equal to 0.13, it is defined as a high PD-1/CD8 ratio. When the ratio of the signal value of the PD-1 to the signal value of the CD8 calculated in the H-score method is less than 0.13, it is defined as a low PD-1/CD8 ratio.

TABLE 9

| | PBMC | | | TIL | | |
|---|---|---|---|---|---|---|
| ID | CD8 | PD-1 | PD-1/CD8 | CD8 | PD-1 | PD-1/CD8 |
| 1 | 2878 | 368 | 0.13 | 648 | 0 | 0.00 |
| 3 | 3410 | 265 | 0.08 | 380 | 0 | 0.00 |
| 4 | 2095 | 830 | 0.40 | 80 | 26 | 0.33 |
| 5 | 4315 | 805 | 0.19 | 753 | 7 | 0.01 |
| 9 | 5890 | 368 | 0.06 | 231 | 3 | 0.01 |
| 10 | 1797 | 202 | 0.11 | 218 | 12 | 0.06 |
| 11 | 5968 | 1303 | 0.22 | 189 | 24 | 0.13 |
| 13 | 4705 | 823 | 0.17 | 195 | 22 | 0.11 |
| 14 | 4970 | 40 | 0.008 | 1068 | 153 | 0.14 |
| 17 | 2740 | 513 | 0.19 | 764 | 185 | 0.24 |
| 19 | 1792 | 965 | 0.54 | 562 | 343 | 0.61 |
| 20 | 3868 | 995 | 0.26 | 381 | 224 | 0.59 |
| 21 | 3045 | 635 | 0.21 | 43 | 0 | 0.00 |

Figure 16:
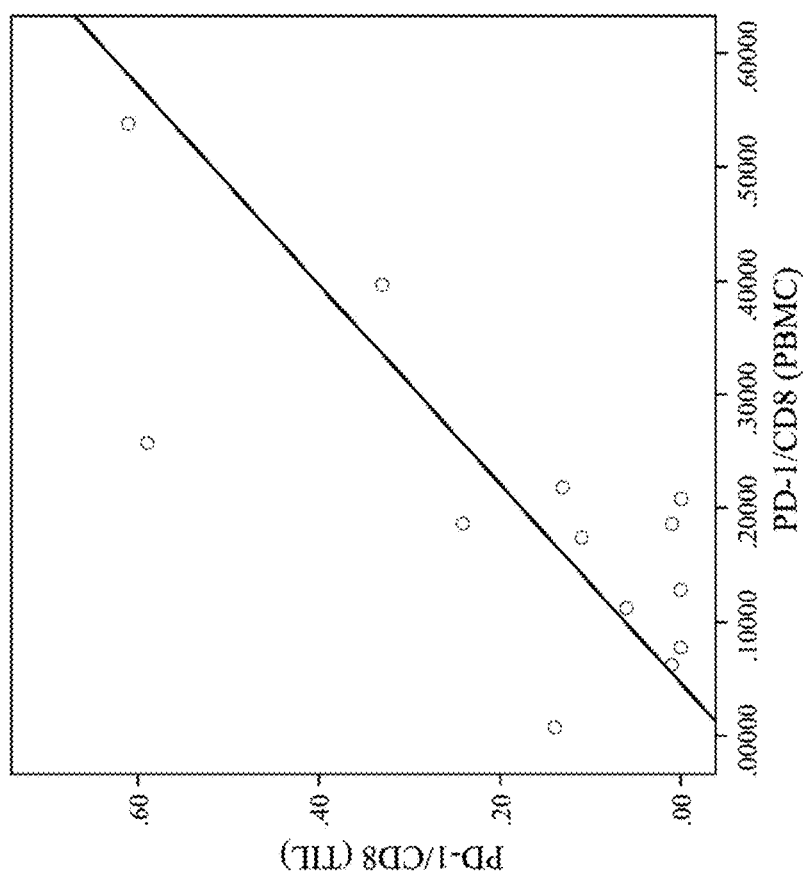
FIG. 16 is a correlation diagram between the ratio of the expression level of the PD-1 to the expression level of the CD8 of peripheral blood mononuclear cells and the ratio of the expression level of the PD-1 to the expression level of the CD8 of tumor infiltrating lymphocytes.

In this example, the immunohistochemistry stained cell block results are further analyzed by the Pearson correlation coefficient to analyze the correlation between the PD-1/CD8 ratio of the PBMC in the GBM patient treated with the dendritic cell tumor vaccine and the PD-1/CD8 ratio of the TIL of in the GBM patient treated with the dendritic cell tumor vaccine. FIG. 16 is the correlation diagram between the PD-1/CD8 ratio of the PBMC in the GBM patient treated with the dendritic cell tumor vaccine and the PD-1/CD8 ratio of the TIL in the GBM patient treated with the dendritic cell tumor vaccine.

TABLE 10

| | | PD-1/CD8 ratio (PBMC) | PD-1/CD8 ratio (TIL) |
|---|---|---|---|
| PD-1/CD8 ratio (PBMC) | Pearson Correlation | 1 | 0.752** |
| | Sig. (two-tailed) | — | 0.003 |
| | number | 13 | 13 |
| PD-1/CD8 ratio (TIL) | Pearson Correlation | 0.752** | 1 |
| | Sig. (two-tailed) | 0.003 | — |
| | number | 13 | 13 |

In FIG. 16 and Table 10, there is the positive correlation between the PD-1/CD8 ratio of the PBMC in the GBM patient treated with the dendritic cell tumor vaccine and the PD-1/CD8 ratio of the TIL in the GBM patient treated with the dendritic cell tumor vaccine. The Pearson correlation coefficient is 0.752; it indicates that there is the statistically significant high correlation between the PD-1/CD8 ratio of the PBMC in the GBM patient treated with the dendritic cell tumor vaccine and the PD-1/CD8 ratio of the TIL in the GBM patient treated with the dendritic cell tumor vaccine. The correlation coefficient between the PD-1/CD8 ratio of the PBMC in the GBM patient treated with the dendritic cell tumor vaccine and the PD-1/CD8 ratio of the TIL in the GBM patient treated with the dendritic cell tumor vaccine is shown in Table 10 as follows. The results of the correlation coefficient analysis suggest that the method of evaluating the GBM patient who is applicable to be treated with the immunotherapy treatment based on the dendritic cell tumor vaccine and the method of prognosticating the survival rate in the GBM patient after the treatment not only can be estimated by measuring the expression level of the biomarker in the tumor tissue but also can be estimated by measuring the expression level of the biomarker in the blood.

4.2 Survival Analysis

13 GBM patients treated with the dendritic cell tumor vaccine are classified into the high expression level of biomarker and the low expression level of the biomarker according to the semi-quantitative analysis, wherein the sample is the blood. Statistical analysis is further performed by using GraphPad PRISM 4.05 (San Diego, Calif., USA) and SAS 9.01. A survival time is analyzed by Kaplan-Meier estimate, and a statistical significant of the survival time is further analyzed by a log rank test. A p-value of <0.05 is considered statistically significant in all statistical analysis of this example.

Figure 17:
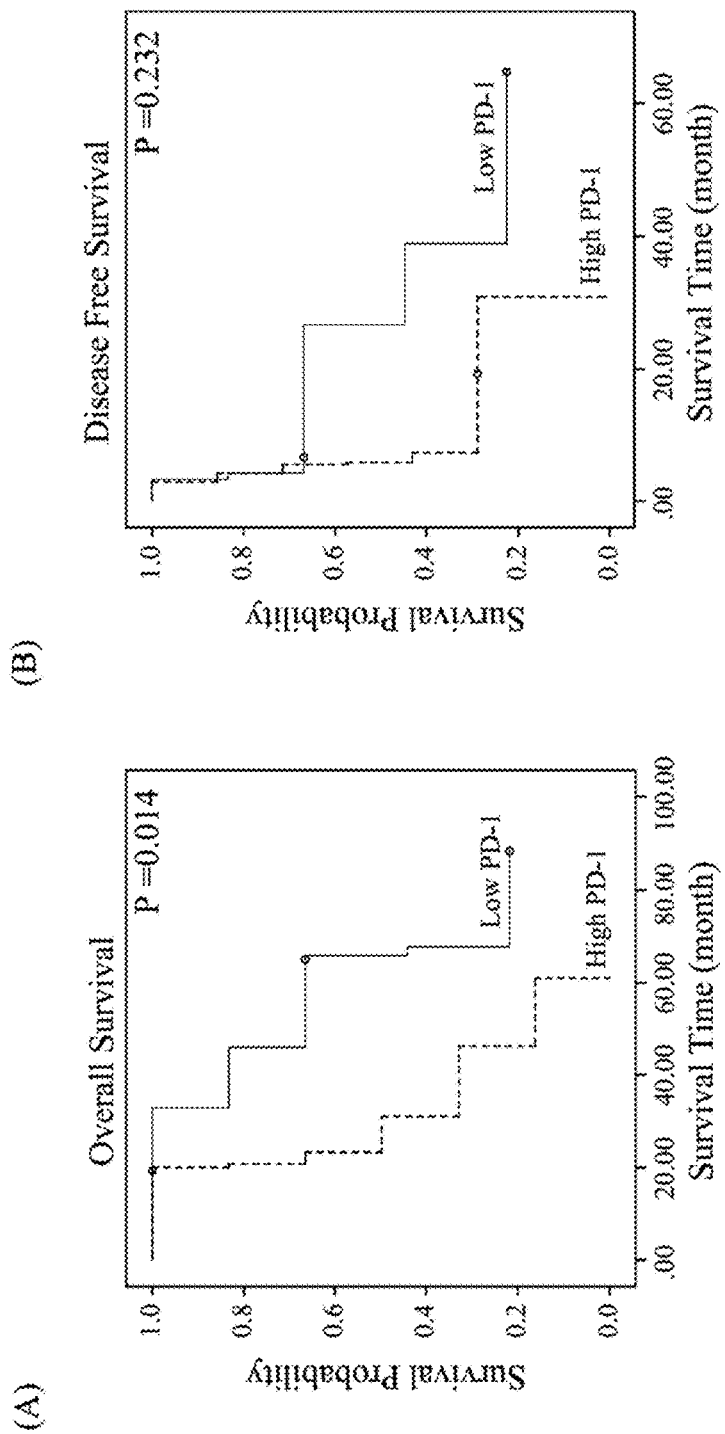
FIG. 17 is a set of the survival curves of the GBM patients treated with the dendritic cell tumor vaccine and further classified based on the expression level of the PD-1 of the peripheral blood mononuclear cells, wherein (A) represents the overall survival curve, (B) represents the disease free survival curve.
Figure 18:
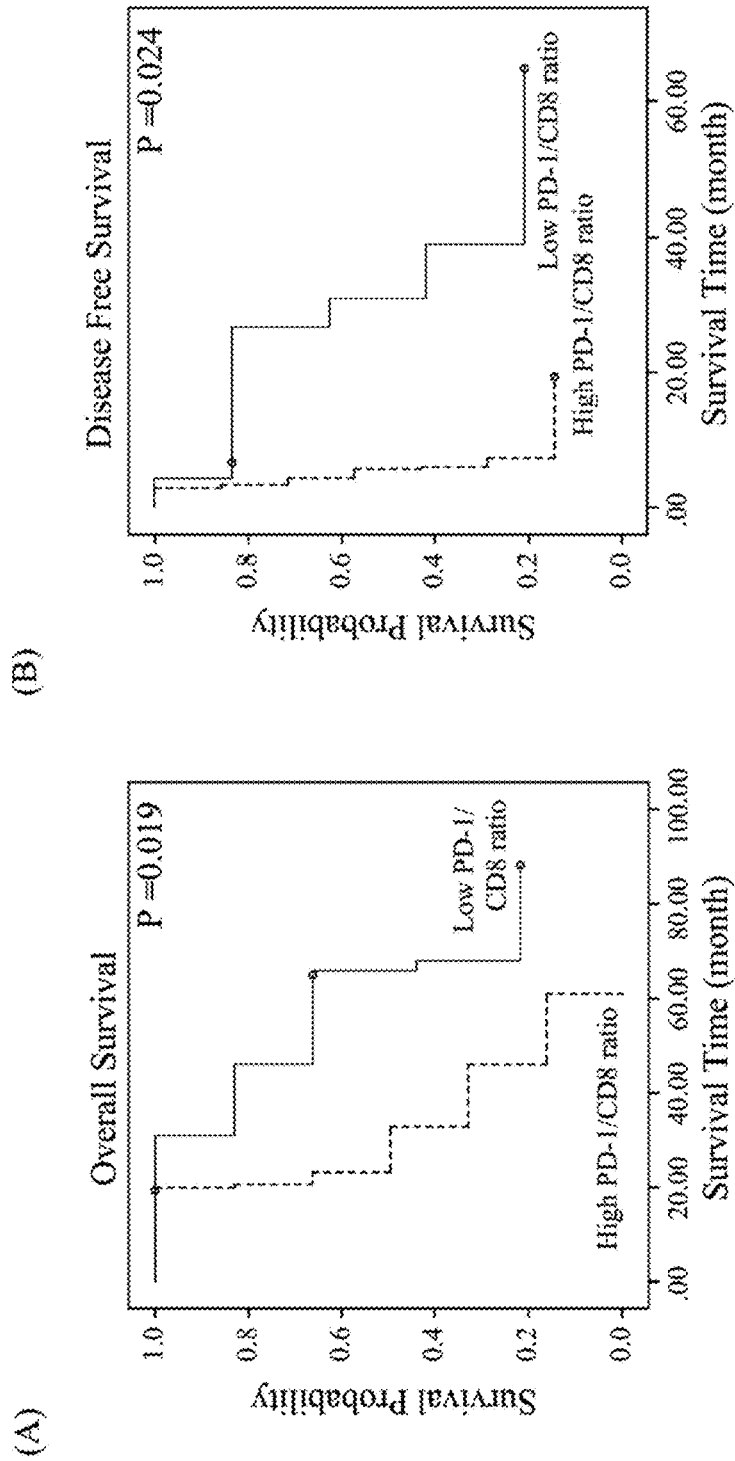
FIG. 18 is a set of the survival curves of the GBM patients treated with the dendritic cell tumor vaccine and further classified based on a ratio of the expression level of the PD-1 to the expression level of the CD8 of the peripheral blood mononuclear cells, wherein (A) represents the overall survival curve, (B) represents the disease free survival curve.

FIG. 17 is a set of the survival curves of the GBM patients treated with the dendritic cell tumor vaccine and further classified based on the expression level of the PD-1 of the PBMC, wherein (A) represents the overall survival curve, (B) represents the disease free survival curve. FIG. 18 is a set of the survival curves of the GBM patients treated with the dendritic cell tumor vaccine and further classified based on the PD-1/CD8 ratio of the PBMC, wherein (A) represents the overall survival curve, (B) represents the disease free survival curve.

In FIG. 17, there is a significant difference (p=0.014) in the overall survival time between the GBM patient who has the low expression level of the PD-1 and the GBM patient who has the high expression level of the PD-1, wherein the GBM patient is treated with the dendritic cell tumor vaccine. There is also the difference (p=0.232) in the disease free survival time between the low expression level of the PD-1 and the high expression level of the PD-1 in the GBM patient treated with the dendritic cell tumor vaccine.

In FIG. 18, when the analysis criteria is the ratio of the expression level of the PD-1 to the expression level of the CD8 (the PD-1/CD8 ratio), the overall survival time in the GBM patient who has the low PD-1/CD8 ratio is longer than that in the GBM patient who has the high PD-1/CD8 ratio, wherein the GBM patient is treated with the dendritic cell tumor vaccine. The p-value is 0.019. The disease free survival time in the GBM patient who has the low PD-1/CD8 ratio is also significant longer than that in the GBM patient who has the high PD-1/CD8 ratio. The p-value is 0.024.

FIGS. 17-18 further indicate that the survival analysis results analyzed from the blood of the GBM patients and the survival analysis results analyzed from the tumor tissue of the GBM patients are the same. It further indicates that the method of evaluating the GBM patient who is applicable to be treated with the immunotherapy treatment based on the dendritic cell tumor vaccine and the method of prognosticating the survival rate in the GBM patient after the treatment can be estimated by measuring the expression level of the biomarker in the blood of the GBM patients.

To sum up, the present disclosure provides the method of evaluating the GBM patient who is applicable to be treated with the immunotherapy treatment based on the dendritic cell tumor vaccine by measuring the expression level of the PD-1 or the expression level of the PD-1, or calculating the PD-1/CD8 ratio in the tumor tissue or the blood. Therefore, the physician can quickly and objectively identify the GBM patient who is applicable to be treated with the immunotherapy treatment based on the dendritic cell tumor vaccine in a clinical application. In this way, the physician can exclude the GBM patient who has no effect on the immunotherapy based on the dendritic cell tumor vaccine to ensure effective distributions and utilizations of medical resources. The present disclosure also provides the method of prognosticating the survival rate in the GBM patient after the treatment by measuring the expression level of the PD-1 or the expression level of the PD-1, or calculating the PD-1/CD8 ratio in the tumor tissue or the blood. The method can be used to predict the survival rate of the GBM patient after the treatment. Therefore, the physician can determine whether the GBM patient need to treat with other drugs or treatment plans to enhance the overall survival time and the disease free survival time in the clinical application.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method of treating a glioblastoma multiforme in a glioblastoma multiforme patient, the method comprising:
    obtaining a sample from the glioblastoma multiforme patient;
    detecting an expression level of PD-1 and an expression level of CD8 by an immunohistochemistry;
    counting a number of PD-1 stained cells and a number of CD8 stained cells by a H-score method;
    summing up the number of the PD-1 stained cells and the number of the CD8 stained cells in 25 high power field to obtain a signal value of PD-1 and a signal value of CD8 respectively;
    calculating a base value by dividing the signal value of PD-1 by the signal value of CD8;
    comparing the base value with a threshold, wherein the threshold is a PD-1/CD8 ratio median in the H-score method; and
    administering an immunotherapy treatment to the glioblastoma multiforme patient whose base value is lower than the threshold.

2. The method of claim 1, wherein the sample is a tumor tissue or a blood.

3. The method of claim 2, wherein the tumor tissue is a tissue section or a tissue microarray.

4. The method of claim 1, wherein the immunotherapy treatment is the immunotherapy treatment based on a dendritic cell tumor vaccine.

5. The method of claim 4, wherein the dendritic cell tumor vaccine is an autologous dendritic cell tumor vaccine.

* * * * *